US008666680B2

(12) United States Patent
Sondermann et al.

(10) Patent No.: US 8,666,680 B2
(45) Date of Patent: Mar. 4, 2014

(54) RECOMBINANT SOLUBLE FC RECEPTORS

(75) Inventors: Peter Sondermann, Krailling (DE); Robert Huber, Germering (DE); Uwe Jacob, München (DE)

(73) Assignee: Max-Planck-Gesellschaft zur Förderung der Wissenschaften e.V. (DE)

( * ) Notice: Subject to any disclaimer, the term of this patent is extended or adjusted under 35 U.S.C. 154(b) by 0 days.

(21) Appl. No.: 13/272,253

(22) Filed: Oct. 13, 2011

(65) Prior Publication Data

US 2012/0190821 A1 Jul. 26, 2012

Related U.S. Application Data

(60) Continuation of application No. 12/381,719, filed on Mar. 16, 2009, now abandoned, which is a division of application No. 11/327,695, filed on Jan. 6, 2006, now Pat. No. 7,504,482, which is a division of application No. 09/856,933, filed as application No. PCT/EP99/09440 on Dec. 3, 1999, now Pat. No. 7,074,896.

(30) Foreign Application Priority Data

Dec. 3, 1998 (EP) ..................................... 98122969

(51) Int. Cl.
*G01N 23/00* (2006.01)

(52) U.S. Cl.
USPC ............................................. 702/27; 436/86

(58) Field of Classification Search
None
See application file for complete search history.

(56) References Cited

U.S. PATENT DOCUMENTS

| | | | |
|---|---|---|---|
| 5,470,578 A | 11/1995 | Aoki et al. |
| 5,623,053 A | 4/1997 | Gastinel et al. |
| 5,856,116 A | 1/1999 | Wilson et al. |
| 5,858,981 A | 1/1999 | Schreiber et al. |
| 6,675,105 B2 | 1/2004 | Hogarth et al. |
| 7,074,896 B1 | 7/2006 | Sondermann et al. |
| 7,504,482 B2 | 3/2009 | Sondermann et al. |
| 2009/0292113 A1 | 11/2009 | Sondermann et al. |
| 2012/0190821 A1 | 7/2012 | Sondermann et al. |

FOREIGN PATENT DOCUMENTS

| | | |
|---|---|---|
| EP | 0 529 615 A1 | 3/1988 |
| EP | 0 319 307 | 6/1989 |

(Continued)

OTHER PUBLICATIONS

Allen, et al. "Isolation and Expression of Functional High-Affinity Fc Receptor Complementary DNAs", *Scie.* 243 (1988) pp. 378-381.

(Continued)

*Primary Examiner* — Nashaat Nashed
(74) *Attorney, Agent, or Firm* — Fulbright & Jaworski LLP

(57) ABSTRACT

Recombinant soluble Fc receptors according to the present invention are characterized by the absence of transmembrane domains, signal peptides and glycoslyation. Such Fc receptors can easily be obtained by expressing respective nucleic acids in prokaryotic host ells and renaturation of the obtained inclusion bodies, which procedure leads to a very homogenous and pure product. The products can be used for diagnostic as well as pharmaceutical applications and also for the generation of crystal structure data. Such crystal structure data can be used for the modeling of artificial molecules. A further embodiment comprises coupling the Fc receptors according to the invention to solid materials like chromatography materials that an be used to separate and/or enrich antibodies.

2 Claims, 14 Drawing Sheets

(56) References Cited

FOREIGN PATENT DOCUMENTS

| EP | 0 321 842 A1 | 6/1989 |
|---|---|---|
| EP | 0 614 978 A1 | 9/1994 |
| EP | 0 791 653 A1 | 8/1997 |
| FR | 2 739 560 A | 4/1997 |
| JP | 07-149800 A | 6/1995 |
| JP | 4914535 B2 | 4/2012 |
| WO | WO 95/09002 A1 | 4/1995 |
| WO | 95/35367 A1 | 12/1995 |
| WO | WO 96/40199 A1 | 12/1996 |
| WO | 98/07835 A2 | 2/1998 |
| WO | WO 99/05271 | 2/1999 |
| WO | WO 99/40117 A1 | 8/1999 |

OTHER PUBLICATIONS

Blank, et al. "Characterization of Trancated α Chain Products from Human, Rat, and Mouse High Affinity Receptor for Immunoglobulin E", *J. Biol. Chem*. 266(4), (1991), pp. 2639-1646.

Fan, et al. "Direct binding of a soluble natural killer cell inhibitory receptor to a soluble human leukocyte antigen-Cw4 class I major histocompatibility complex molecule", *Proc. Nat. Acad. Aci. USA*, 93 (1996), pp. 7178-7183.

Galon, et al. "Affinity of the interaction between Fc gamma receptor type III (FcγRIII) and monomeric human IgG subclasses., Role of FcγRIIIglycosylation.", *Eur. J. Immunol*. 27 (1997), pp. 1928-1932.

Gao, et al. "Assembly and crystallization of the complex between the human T cell coreceptor CD8α homodimer and HLA-A2", *Protein Sci*. 7 (1998), pp. 1245-1249.

Grueninger-Leitch, et al. "deglycosylation of proteins for crystallization using recombinant fusion protein glycosylation."*Protein Sci*. 5 (1998), pp. 2617-2622.

Malchiodi, et al. "Superantigen Binding to a T Cell Receptor β Chain of Known Three-dimentional Structure." *J. Exp. Med*.182 (1995), pp. 1833-1845.

Sondermann, et al. "Crystal structure of the soluble form of the human Fcγ-receptor llb: a new member of the immunoglobulin superfamily at 1.7 Å resolution." *EMBO J*. 18(5), (1999), pp. 1095-1103.

Sondermann, et al. "Human Fcγ Receptor llb Expressed in *Escherichia coli* Reveals IgG Binding Capability." *Biol. Chem*. 380 (1999), pp. 717-721.

Stoyan, et al. "Recombinant soluble human interleukin-6 receptor. Expression in *Escherichia coli*, renaturation and purification." *Eur. J, Biochem*. 216 (1993), pp. 239-245.

Cohlovius, et at. "Therapeutic Antibodies", *Modem Drugs Disc.*. (2003) pp. 33-38.

Cohen, et al, "Molecular Modeling Software and Methods for Medicinal Chemistry", *J.Med. Chem*. 33 No. 3 (1990), pp. 883-894.

Feldman, et al. "Anti-TNFα Therapy Is Useful in Rheumatoid Arthritis and Crohn's Disease: Analysis of the Mechanism of Action Predicts Utility in Other Diseases", *Transplant. Proceed*. 20 (1998), pp. 4128-24127.

Galon, et al. "Ligands and niological activities of soluble Fcγ receptors", *Immunol. Let*. 44 (1995), pp. 175-181.

Gastinel, et al. "Expression and crystallization of a soluble and functional form of an Fc receptor related to class I histocompatibility molecules", *Proc. Natl. Acad. Sci. USA* 89 (1992), pp. 638-642.

Lazar, et al. "Transforming Growth Factor α: Mutation of Asparic Acid 47 and Leucine 48 Results in Different Biological Activities", *Mol. Cel. Biol*. 8 No. 3 (1988), pp. 1247-1252.

Maxwell, et al. "Crystal structure of the human leukocyte Fc receptor, FcγRlla", *nat. Struct. Biol*. 6 No. 5, pp. 437-442, (1999).

Mikayama, et al. "Molecular cloning and functional expression of a cDNA encoding glycosylation-inhibiting factor", *Proc. Natl. Acad. Sci. USA* 90 (1993), pp. 10056-10060.

Powell. et al. "Biochemical analysis and crystallisation of FcγRlla, the low affinity receptor for IgG", *Immunol. Let*. 68 (1999), pp. 17-23.

Sondermann, et al. "Characterization and Crystallization of Soluble Human Fcγ Receptor II (CD32) Isoforms Produced in Insect Cells", *Biochem*. 38 (1999) pp. 8469-8477.

Sondermann, et al. "The 3.2. Å crystal structure of the human IgG1 Fc fragment-FcγRlll complex", *Nature* 406 (2000), pp. 267-273.

Sutter, et al. "Nonlinear Optical and Electrooptical Effect in 2-Methil-4-Nitro-N-Methylaniline (MNMA) Crystals", *J. Quantum El*. 24 No. 12, pp. 2362-2366, (1988).

Yang, et al. "Distinct Cellular interactions of Secreted and Transmembrane Ebola Virus Glycoproteins", *Sci*. 279 (1998), pp. 1034-1037.

Burgess, et al. "Possible Dissociation of the Heparin-binding and Mitogenic Activities of Heparin-binding (Acidic Fibroblast) growth Factor-1 from Its Receptor-binding Activities by Site-directied Mutagenesis of a Single Lysine Residue", *J. Cell Biol*. 111 (1999). pp. 2129-2138.

Burmeister, et al. "Crystal structure at 2.2 Å resolution of the MHC-related neonatal Fc receptor", *Nature* 372 (1994) pp. 336-343.

Burmeister, et al. "Crystal structure of the complex of rat neonatal Fc receptor with Fc", *Nature* 372 (1994) pp. 379-383.

Alignment of the Produced sFcγR, sFcεRIa and the short form of sFcεRII

| | | |
|---|---|---|
| sFcγRIIa | ---MAAPPKAVLKLEPP-WINVLQEDSVTLTCQGARSPESDSIQWFHN-GNLIPTHTQPS | 1st aa 1-55 of SEQ ID NO: 2 |
| sFcγRIIb | MGTPAAPPKAVLKLEPQ-WINVLQEDSVTLTCRGTHSPESDSIQWFHN-GNLIPTHTQPS | 2nd aa 1-58 of SEQ ID NO: 3 |
| sFcγRIII | -MRTEDLPKAVVFLEPQ-WYSVLEKDSVTLKCQGAYSPEDNSTQWFHN-ESLISSQASSY | 3rd aa 1-57 of SEQ ID NO: 4 |
| sFcγRI | --------MAVISLQPP-WVSVFQEETVTLHCEVLHLPGSSSTQWFLN-GTATQTSTPSY | 4th aa 1-50 of SEQ ID NO: 1 |
| sFcεRIa | ---MAVPQKPKVSLNPP-WNRIFKGENVTLTCNGNNFFEVSSTKWFHN-GSLSEETNSSL | 5th aa 1-55 of SEQ ID NO: 5 |
| sFcεRII | -MELQVSSGFVCNTCPEKWINFQRK------C---YYFGKGTKQWVHARYACDDMEGQLV | 6th aa 104-153 of SEQ ID NO: 6 |

| | | |
|---|---|---|
| sFcγRIIa | YRFKANNNDSG-EYTCQTGQTSLSDPVHLTVLSEWLV-LQTPHLEFQEGETIHLRCHSWK | 1st aa 56-113 of SEQ ID NO: 2 |
| sFcγRIIb | YRFKANNNDSG-EYTCQTGQTSLSDPVHLTVLSEWLV-LQTPHLEFQEGETIVLRCHSWK | 2nd aa 59-116 of SEQ ID NO: 3 |
| sFcγRIII | FIDAATVNDSG-EYRCQTNLSTLSDPVQLEVHIGWLL-LQAPRWVFKEEDPIHLRCHSWK | 3rd aa 58-115 of SEQ ID NO: 4 |
| sFcγRI | RITSASVNDSG-EYRCQRGLSGRSDPIQLEIHRGWLL-LQVSSRVFTEGEPLALRCHAWK | 4th aa 51-108 of SEQ ID NO: 1 |
| sFcεRIa | NIVNAXFEDSG-EYKCQHQQVNESEPVYLEVFSDWLL-LQASAEVVMEGQPLFLRCHGWR | 5th aa 56-113 of SEQ ID NO: 5 |
| sFcεRII | SIHSPEEQDFLTKHASHTGSWIGLRWLDLKGEFIWVDGSHVDYSNWAPGEPTS-RSQGED | 6th aa 154-212 of SEQ ID NO: 6 |

| | | |
|---|---|---|
| sFcγRIIa | DKPLVKVTFFQNGK-SQXFSRLDPTFSIPQANNSHSGDYHCTGNIGYTLFSSKPVTITVQ | 1st aa 114-172 of SEQ ID NO: 2 |
| sFcγRIIb | DKPLVKVTFFQNGK-SKKFSRSDPNFSIPQANNSHSGDYHCTGNIGYTLYSSKPVTITVQ | 2nd aa 117-175 of SEQ ID NO: 3 |
| sFcγRIII | NTALHKVTYLQNGK-DRKYFHHNSDFHIPKATLKDSGSYFCRGLVGSKNVSSETVNITIT | 3rd aa 116-174 of SEQ ID NO: 4 |
| sFcγRI | DKLVYNVLYYRNGK-AFKFFHWNSNLTILKTNISHNGTYHCSG-MGKHRYTSAGISVTVK | 4th aa 109-166 of SEQ ID NO: 1 |
| sFcεRIa | NWDVYKVIYYKDGE-ALKYWYENHNISITNATVEDSGTYYCTGKVWQLDYESEPLNITVI | 5th aa 114-172 of SEQ ID NO: 5 |
| sFcεRII | CVHMRGSGRWNDAFCDRKLGAWVCDRLATCTPPASEGSAESHGPDSRPDPDGRLPTPSAP | 6th aa 213-272 of SEQ ID NO: 6 |

| | | |
|---|---|---|
| sFcγRIIa | VP-------------------------------------------------------- | 1st aa 173-174 of SEQ ID NO: 2 |
| sFcγRIIb | APSSSPMGII------------------------------------------------ | 2nd aa 176-185 of SEQ ID NO: 3 |
| sFcγRIII | OG-------------------------------------------------------- | 3rd aa 175-176 of SEQ ID NO: 4 |
| sFcγRI | ELFPAPVLNASVTSPLLEGNLVTLSCETKLLLQRPGLQLYFSFYHGSKTLRGRNTSSEYQ | 4th aa 167-226 of SEQ ID NO: 1 |
| sFcεRIa | KAPREXYWLQF----------------------------------------------- | 5th aa 173-183 of SEQ ID NO: 5 |
| sFcεRII | LHS------------------------------------------------------- | 6th aa 273-275 of SEQ ID NO: 6 |

| | | |
|---|---|---|
| sFcγRIIa | ------------------------------------------ | |
| sFcγRIIb | ------------------------------------------ | |
| sFcγRIII | ------------------------------------------ | |
| sFcγRI | ILTARREDSGLYWCEAATEDGNVLKRSPELELQVLGLQLPTPV | aa 227-269 of SEQ ID NO: 1 |
| sFcεRIa | ------------------------------------------ | |
| sFcεRII | ------------------------------------------ | |

FIG. 11

Alignment the Produced sFcγR and sFcεRIa without sFcεRII

```
sFcγRIIa    ---MAAPPKAVLKLEPPWINVLQEDSVTLTCQGARSPESDSIQWFHNGNLIPTHTQPSYR   1st aa 1-57 of SEQ ID NO: 2
sFcγRIIb    MGTPAAPPKAVLKLEPQWINVLQEDSVTLTCRGTHSPESDSIQWFHNGNLIPTHTQPSYR   2nd aa 1-60 of SEQ ID NO: 3
sFcγRIII    -MRTEDLPKAVVFLEPQWYSVLEKDSVTLKCQGAYSPEDNSTQWFHNESLISSQASSYFI   3rd aa 1-59 of SEQ ID NO: 4
sFcγRI      --------MAVISLQPPWVSVFQEETVTLHCEVLHLPGSSSTQWFLNGTATQTSTPSYRI   4th aa 1-52 of SEQ ID NO: 1
sFcεRIa     ---MAVPQKPKVSLNPPWNRIFKGENVTLTCNGNNFFEVSSTKWFHNGSLSEETNSSLNI   5th aa 1-57 of SEQ ID NO: 5
               . :*:* *  ::: :.*** *.         .* :** * .

sFcγRIIa    FKANNNDSGEYTCQTGQTSLSDPVHLTVLSEWLVLQTPHLEFQEGETIMLRCHSWKDKPL   1st aa 58-117 of SEQ ID NO: 2
sFcγRIIb    FKANNNDSGEYTCQTGQTSLSDPVHLTVLSEWLVLQTPHLEFQEGETIVLRCHSWKDKPL   2nd aa 61-120 of SEQ ID NO: 3
sFcγRIII    DAATVNDSGEYRCQTNLSTLSDPVQLEVHIGWLLLQAPRWVFKEEDPIHLRCHSWKNTAL   3rd aa 60-119 of SEQ ID NO: 4
sFcγRI      TSASVNDSGEYRCQRGLSGRSDPIQLEIHRGWLLLQVSSRVFTEGEPLALRCHAWKDKLV   4th aa 53-112 of SEQ ID NO: 1
sFcεRIa     VNAKFEDSGEYKCQHQQVNESEPVYLEVFSDWLLLQASAEVVMEGQPLFLRCHGWRNWDV   5th aa 58-117 of SEQ ID NO: 5
             *  :***** **      *:*: * :   **:**..  . * :.: ****.*:: :

sFcγRIIa    VKVTFFQNGKSQKFSRLDPTFSIPQANHSHSGDYHCTGNIGYTLFSSKPVTITVQVP---   1st aa 118-174 of SEQ ID NO: 2
sFcγRIIb    VKVTFFQNGKSKKFSRSDPNFSIPQANHSHSGDYHCTGNIGYTLYSSKPVTITVQAPSSS   2nd aa 121-180 of SEQ ID NO: 3
sFcγRIII    HKVTYLQNGKDRKYFHHNSDFHIPKATLKDSGSYFCRGLVGSKNVSSETVNITITQG---   3rd aa 120-176 of SEQ ID NO: 4
sFcγRI      YNVLYYRNGKAFKFFHWNSNLTILKTNISHNGTYHCSG-MGKHRYTSAGISVTVKELFPA   4th aa 113-171 of SEQ ID NO: 1
sFcεRIa     YKVIYYKDGEALKYWYENHNISITNATVEDSGTYYCTGKVWQLDYESEPLNITVIKAPRE   5th aa 118-177 of SEQ ID NO: 5
             :* : ::*: *:    :  : * ::. ...* *.* *      *  :..:*:

sFcγRIIa    --------------------------------------------------
sFcγRIIb    PMGII---------------------------------------------   aa 181-185 of SEQ ID NO: 3
sFcγRIII    --------------------------------------------------
sFcγRI      PVLNASVTSPLLEGNLVTLSCETKLLLQRPGLQLYFSFYMGSKTLRGRNTSSEYQILTAR   aa 172-231 of SEQ ID NO: 1
sFcεRIa     KYWLQF--------------------------------------------   aa 178-183 of SEQ ID NO: 5 sFcγRIIa    --------------------------------------
sFcγRIIb    --------------------------------------
sFcγRIII    --------------------------------------
sFcγRI      REDSGLYWCEAATEDGNVLKRSPELELQVLGLQLPTPV   aa 232-269 of SEQ ID NO: 1
sFcεRIa     --------------------------------------
```

FIG. 12

RECOMBINANT SOLUBLE FC RECEPTORS

This application is a continuation application of U.S. Ser. No. 12/381,719 filed Mar. 16, 2009, abandoned, which is a divisional application of U.S. Ser. No. 11/327,695 filed Jan. 6, 2006, now U.S. Pat. No. 7,504,482, which is a divisional application of U.S. Ser. No. 09/856,933 filed Feb. 27, 2002 now U.S. Pat. No. 7,074,896, which is a §371 of PCT/EP99/09440, filed Dec. 3, 1999, each of which is incorporated herein by reference in its entirety.

The present invention relates to recombinant soluble Fc receptors (FcR), recombinant nucleic acids coding for such Fc receptors, host cells containing corresponding nucleic acids as well as a process for the determination of the amount of antibodies of a certain type contained in the blood, plasma or serum of a patient, a process for the determination of the immune status of patients with chronic diseases of the immune system and a process for the screening of substances in view of their ability to act as inhibitors of the recognition and binding of antibodies to the respective cellular receptors. Further, the present invention is concerned with pharmaceutical compositions containing the recombinant soluble Fells, crystalline preparations of FcRs and FcR/Ig-complexes and especially of the use of such crystalline preparation for the generation of crystal structure data of Fc receptors as well as FcR inhibitors and pharmaceutical compositions containing such FcR inhibitors.

A still further subject of the present invention is a recombinant Fc receptor coupled to a solid phase, e.g. a chromatography carrier material. The use of such chromatography material, which is another subject of the present invention, lies in the absorption of immunoglobulins from a body fluid of patients or from culture supernatants of immunoglobulin producing cells.

Fc receptors (FcRs) play a key role in defending the human organism against infections. After pathogens have gained access to the blood circulation they are opsonized by immunoglobulins (Igs). The resulting immunocomplexes bind due to their multivalency with high avidity to FcR bearing cells leading to clustering of the FcRs, which triggers several effector functions (Metzger, H., 1992A). These include, depending on the expressed FcR type and associated proteins, endocytosis with subsequent neutralization of the pathogens and antigen presentation, antibody-dependent cellular cytotoxity (ADCC), secretion of mediators or the regulation of antibody production (Fridman et al 1992; van de Winkel and Capel, 1993).

Specific FcRs exist for all Ig classes, the ones for IgG being the most abundant with the widest diversity. Together with the high affinity receptor for IgE (FcεRIa), FcγRI (CD64), FcγRII (CD32) and FcγRIIIa (CD16) occur as type I transmembrane proteins or in soluble forms (sFcRs) but also a glycosylphosphatidylinositol anchored form of the FcγRII (FcγRIIIb) exists. Furthermore, FcγRs occur in various isoforms (FcγRIa, b1, b2, c; FcγRIIa-1-2, b1-3, c) and alleles (FcγRIIa1-HR, -LR; FcγRIIIb-NA1, -NA2) (van de Winkel and Capel, 1993). In contrast to the overall homologous extracellular parts, the membrane spanning and the cytoplasmic domains differ. They may be deleted entirely or be of a size of 8 kDa. They may contain either a 26 amino acid immunoreceptor tyrosine-based activation motif (ITAM) as in FcγRIIa or a respective 13 amino acid inhibitory motif (ITIM) in FcγRIIb involved in signal transduction (Amigorena et al, 1992).

Judged by the conserved spacing of cysteines, the extracellular part of the FcRs consists of three (FcγRI, CD64) or two (FcεRI, FcγRII, CD32 and FcγRIII, CD16) Ig-like domains (10 kDa/domain) and therefore belongs to the immunoglobulin super family. These highly glycosylated receptors are homologues, and the overall identity in amino acid sequence among the FcγRs and FcεRIa exceeds 50% in their extracellular regions. Nevertheless, the affinity of FcRs to their ligands varies widely. The higher affinity of $\sim 10^8 M^{-1}$ of the FcγRI to Fc-fragment is assigned to its third domain, while the other FcγRs with two domains have an affinity to IgG varying between $10^5$ and $10^7 M^{-1}$. The affinity of the two domain FcεRIa to IgE exceeds these an values by far with a constant of $10^{10} M^{-1}$ (Metzger, H, 1992B). In contrast to the mentioned FcRs the low affinity receptor for IgE FcεRII represents a type transmembrane protein and shows a lower homology.

FcγRs are expressed in a defined pattern on all immunological active cells. FcγRI is constitutively expressed on monocytes and macrophages and can be induced on neutrophils and eosinophils. The physiological role of FcγRI is still unknown as the expression on monocytes is not vital (Ceuppens at al, 1988). The GPI anchored form of FcγRII (FcγRIIIb) is exclusively expressed on granulocytes. Due to its missing cytoplasmic part, the signal transduction into the cell occurs solely via other transmembrane proteins like complement receptor type 3 (CR3) that can at least associate with FcγRIIIb (Zhou at al, 1993; Poo at al, 1995). FcγRIIIa is mainly expressed on monocytes and macrophages but only in conjunction with associated proteins (e.g. α- or γ-chains). FcγRII is the receptor with the widest distribution on immunocompetent cells and is mainly involved in the endocytosis of immunocomplexes.

FcγRIIa and FcγRIIb differ in their extracellular region by only 7% of the amino acid residues. Nevertheless, both forms can be distinguished by their binding characteristics to human and mouse IgG subclasses (van de Winkel and Capel, 1993) and their differing affinity to human IgGs (Sondermann at al, 1998A). The situation is rendered even more complicated by the high responder/low responder (HR/LR) polymorphism of FcγRIIa named after the ability of T cells from some individuals to respond to murine IgG1-induced mitogenesis (Tax at al, 1983). Later, it was found that the two exchanges in the amino acid sequence between the LR and the HR form modify the ability to bind human IgG2, which leads to the suggestion that at least one of them is involved in IgG binding (Hogarth et al, 1992).

In contrast to the beneficial role FcRs play in the healthy individual, they also transmit the stimulation of the immune system in allergies (FcεRIa) or autoimmune diseases. Moreover, some viruses employ FcγRs to get access to cells like HIV (Homsy et al, 1989) and Dengue (Littaua at al, 1990) or slow down the immune response by blocking FcγRs as in the case of Ebola (Yang at al, 1998) and Measles (Ravanel at al, 1997).

Hence, the object underlying the present invention was to provide receptors which are easy to produce and can advantageously be used for medical or diagnostic applications. Moreover, it was an object of the invention to provide soluble receptors exhibiting a binding specificity and activity which is analogous to that of the receptors occurring naturally in the human body and which, additionally, make it possible to produce crystals suitable for a structure determination.

This object is accomplished by recombinant soluble Fc receptors which consist only of the extracellular portion of the receptor and are not glycosylated. The receptors according to the present invention are therefore characterized by the absence of transmembrane domains, signal peptides and glycosylation.

Particularly preferred for the present invention are Fcγ or Fcε receptors. This is because IgG and IgE molecules are characteristic for a multiplicity of diseases and conditions, so that their determination and possible ways of influencing them are of great interest. FIGS. 11 and 12 show an alignment of amino acid sequences of the extracellular parts of some FcγRs and FcεRI. The FcRs according to the invention include all these sequences or parts thereof that still retain binding capacity to antibodies and/or proper crystallization.

In a particularly preferred embodiment of the invention the recombinant soluble FcR is a FcγRIIb receptor. Further, it is particularly preferred that the receptor be of human origin. In a particularly preferred embodiment, it contains an amino acid sequence as shown in one of SEQ ID NO:1 to SEQ ID NO:6.

According to the present invention, the preparation of the soluble Fc receptors preferably takes place in prokaryotic cells. After such expression, insoluble inclusion bodies containing the recombinant protein form in prokaryotic cells, thus facilitating purification by separation of the inclusion bodies from other cell components before renaturation of the proteins contained therein takes place. The renaturation of the FcRs according to the present invention which are contained in the inclusion bodies can principally take place according to known methods. The advantage of the preparation in prokaryotic cells, the production of inclusion bodies and the thus obtained recombinant soluble Fc receptors make it possible to obtain a very pure and, in particular, also very homogeneous FcR preparation. Also because of the absence of glycosylation the obtained product is of great homogeneity.

Soluble Fc receptors hitherto produced by recombinant means particularly exhibited the disadvantage that a much more elaborate purification was required, since they were expressed in eukaryotic cells and, due to the glycosylation which is not always uniform in eukaryotic cells, these products were also less homogeneous.

The recombinant soluble Fc receptors according to the present invention even make it possible to produce crystals suitable for use in X-ray analysis, as shall be explained later on in the description of further embodiments of the invention. The FcRs of the present invention moreover exhibit practically the same activity and specificity as the receptors naturally occurring in vivo.

A further subject matter of the present invention is a recombinant nucleic acid having a sequence coding for a recombinant soluble Fc receptor according to the present invention.

The nucleic acid according to the present invention may contain only the coding sequences or, additionally, vector sequences and/or, in particular, expression control sequences operatively linked to the sequence encoding the recombinant FcR, like promoters, operators and the like.

In a particularly preferred embodiment the nucleic acid of the present invention contains a sequence as shown in one of SEQ ID NO:7 to SEQ ID NO:12. For a comparison, SEQ ID NO:13 and SEQ ID NO:14 show the respective wild type sequences coding for FcγRIIb and FcεRIa. SEQ ID NOs:15-18 show the wild type sequences for FcγRI, FcγRIIa, FcγRII and FcεRII.

If the nucleic acid of the present invention contains vector sequences, then these are preferably sequences of one or several prokaryotic expression vectors, preferably of pET vectors. Any other known functions or components of expression vectors may also be contained in the recombinant nucleic acid according to the present invention if desired. These may, for instance, be resistance genes allowing for an effective selection of transformed host cells.

A still further subject matter of the present invention is a host cell containing a recombinant nucleic acid according to the present invention. As repeatedly mentioned above, the host cell preferably is a prokaryotic host cell, particularly an E. coli cell.

The recombinant soluble Fc receptors according to the present invention can be used for a multitude of examinations or applications because they specifically react with antibodies. In vivo, the soluble Fc receptors are powerful immunoregulators which, if present in elevated levels, result in a remarkable suppression of the immune system which leads to many partly known and partly not yet understood effects. Based on these effects, several applications of the Fc receptors according to the present invention are further subject matters of the present invention.

One such subject is a process for the determination of the amount of antibodies of a certain type in the blood or serum of a patient, which is characterized by the use of a recombinant soluble FcR according to the invention in an immunoassay, and the determination of the presence of FcR-antibody complexes. Such assay allows to screen for the presence of a certain kind of antibody and allows also for the determination of the amount of antibodies present in the blood, plasma or serum of a patient.

Any type of immunoassay is principally suitable for the use according to the present invention, as long as the presence of FcR-antibody complexes can thereby be detected. Both ELISA (enzyme-linked immunosorbent immunoassay), particularly sandwich assays, and RIA (radio-immunoassay) are suitable, but also competitive testing methods. In a preferred embodiment of the invention where the presence and/or the amount of IgE antibodies is to be examined, an FcεR is used as recombinant soluble receptor according to the present invention. In particular, this method is suited and advantageous for determining a predisposition or manifestation of an allergy.

Moreover, a method is preferred in which the presence of soluble FcRs is to be determined and, if required, quantified. For such determination preferably a competitive immunoassay method is used, wherein as competition reagent a recombinant soluble receptor according to the invention is used, most preferably a recombinant FcγR. By means of this test among others the immune status of patients with chronic diseases of the immune system can be determined in a competitive immunoassay. Chronic diseases in the sense of these processes are for instance AIDS, SLE (systemic lupus erythematosus), MM (multiple myeloma) or rheumatoid arthritis, or in the case of FcεRII in B-CLL (Gordon at al., 1987), hyper IgE syndrome (Sarfati at al., 1988) or HCL (Small at al., 1990).

A further advantageous use of the recombinant receptor according to the present invention lies in the screening of substances in view of their ability to act as inhibitors of the recognition and binding of antibodies to the respective cellular receptors.

By means of modern screening techniques such as HTPS (high throughput screening) in combination with multi-well microtiter plates and automatic pipetting apparatuses it is nowadays possible to simultaneously test a multitude of substances for specific properties. As the FcRs according to the present invention can be easily produced at low cost, they can also be used in such series tests by which substances having an inhibiting effect can easily be identified.

Particularly preferred is such use according to which Fc receptors according to the present invention are used to find or screen inhibitors capable of inhibiting the recognition and binding of the respective antibodies to the particular receptor of interest.

A further area of application of the substances according to the invention lies in the pharmaceutical field. Hence, a further subject matter of the invention is a pharmaceutical composition comprising as active agent a recombinant soluble FcR according to the invention. According to the present invention, this pharmaceutical composition may of course comprise conventional useful carrier and auxiliary substances. Such substances are known to the person of skill in the art, the mode of administration also having to be taken into account. The pharmaceutical composition of the present invention can be advantageously used for the treatment or prevention of autoimmune diseases, allergies or tumor diseases.

Soluble forms of Fc receptors such as FcγRIII mediate isotype-specific regulation of B cell growth and immunoglobulin production. In a murine model of myeloma, sFcR suppresses growth and immunoglobulin production of tumor cells (Müller et al, 1985; Roman et al, 1988; Teillaud et al, 1990). Furthermore, sFcR binds to surface IgG on cultures of human IgG-secreting myeloma cells and effects suppression of tumor cell growth and IgG secretion. Prolonged exposure of these cells to sFcR results in tumor cell cytolysis (Hoover et al, 1995).

Also, overreactions of the immune system in allergic reactions or due to massive antigen load might be reduced by, for example, intravenous application of soluble FcR (Ierino et al, 1993).

Therefore, a preferred pharmaceutical composition according to the invention for use in the treatment of AIDS, rheumatoid arthritis or multiple myeloma contains a recombinant soluble Fcγ receptor and, preferably, a receptor having the amino acid sequence as shown in SEQ ID NO:1-4.

It was also of great interest to obtain crystal structure data of Fc receptors and/or Fc receptor/Ig complexes. On the one hand, these are a key to the understanding of molecular mechanisms in immunocomplex recognition. On the other hand, these structural data can be used to find out common features in the structures of different Fc receptors and use the knowledge of the structures to generate inhibitors or identify and produce new artificial antibody receptors.

It was also of great interest to obtain information on the concrete binding sites of immunoglobulins to their respective receptors in naturally occurring three-dimensional molecules. Therefrom even more precise findings on the interactions between antibody and receptor can be obtained and also on how these interactions can be modulated. In this connection modulation means either an enhancement of the interaction or a reduction leading to an inhibition by e.g. covering the binding sites on one or more parts of the complex.

To obtain such crystal structure data and conformation information, a crystalline preparation of the recombinant soluble Fc receptor according to the invention is used. The recombinant soluble FcRs according to the invention surprisingly can be obtained pure enough to produce crystals that give reliable X-ray structure determination data. Such crystallization was not possible with the hitherto produced receptor molecules, mostly due to their lack of homogeneity.

Therefore, another embodiment of the present invention concerns a crytalline preparation of an Fc receptor according to the invention. Vet another embodiment of the present invention is a crystalline preparation of a complex of soluble Fc receptor according to the invention together with the related immunoglobulin Fc part. Particulary preferred embodiments are shown in the examples as well as the relevant crystal structure data. Via crystal structure analysis of the crystalline preparations the exact amino acids of the Fc receptor/Ig complexes could be detected which mediate the coupling. These amino acids are in shown FIGS. 6a and 6b and the type of binding between the individual amino acids of both molecules in the complex is also indicated. A further embodiment of the present invention is therefore the use of a crystalline preparation of a recombinant soluble Fc receptor for the generation of crystal structure data of Fc receptors. From this crystal structure data information about the three-dimensional structure and the active sites for the binding of antibodies can be obtained. Especially preferably is the use of a crystalline preparation of a complex of recombinant soluble Fc receptor according to the invention and the corresponding immunoglobulin molecule for the generation of crystal structure data for the complexes. These data allow to determine the actual interactions that are formed between the two molecules and allow for the first time to obtain exact information about the interaction of the molecules thereby conferring knowledge about possible sites for inhibition or enhancement of the binding. On the basis of the information obtained from the crystal structure data the findings necessary for effecting modulation of the interaction between Fc receptor and immunoglobulin can be obtained. This modulation can be range from enhancement to complete inhibition to an inhibition of the binding.

The stated applications are merely preferred embodiments of the use of the crystal structure data. Many other applications seem possible, too.

Suitably, the structural data for the generation and/or identification of inhibitors or new receptors, respectively, are used in a computer-aided modelling program.

Particularly preferred for the present invention are the structures of FcRs or FcR:Fc-fragment complexes as exemplified in figures and examples. Such structures can be used to design inhibitors, antagonists and artificial receptor molecules.

Computer programs suitable for computer-aided drug design and screening are known to the person skilled in the art and generally available. They provide the possibility to examine umpteen compositions on the computer in view of their ability to bind to a certain molecule when the corresponding structure dates are entered in the computer. With the help of this possibility a great number of known chemical compositions can be examined regarding their inhibiting or antagonistic effect. The person skilled in the art merely requires the crystal structure dates provided by the present invention and a commercially available screening program (Program Flexx: From the GMD-German National Research Center for Information Technology, Schloss Birlinghoven, D-53754 Sankt Augustin, Germany). A preferred embodiment of the present invention therefore is the use of the crystal structure data obtained for the recombinant soluble Fc receptor according to the invention and for the complexes of recombinant soluble Fc receptor according to the invention and corresponding immunoglobulin in a computer aided modelling program for the identification and production of Fc receptor inhibitors.

Likewise, a further embodiment of the present invention is the use of the crystal structure data obtained for the receptors according to the invention and the receptor/immunoglobulin complexes, respectively for the identification and preparation of new Fc receptors which can be used, e.g. as antagonists and competitors. The crystal structure data and the data on the amino acids involved in the binding to Fc receptors obtained therefrom can serve for example to generate mutated immunoglobulins which can also be used as inhibitors. It is imaginable that mutated or chemically modified inhibitors undergo tight binding and thus effect a blocking of receptors. On the other hand, the data obtained for the binding sites of immunoglobulins can also be used for the identification and/or preparation of inhibitors for immunoglobulin molecules.

Since the present invention teaches the binding sites to the receptor, it is easy to effect a blocking of the binding sites with the help of relatively simple molecules. Therefore, a further subject matter of the present invention is the use of the crystal structure data obtained for the FcR/Ig complexes for the identification and/or preparation of immunoglobulin inhibitors.

Accordingly, still further subject matter of the present invention are FcR inhibitors which have a three-dimensional structure which is complementary to the recombinant soluble FcR according to the invention and inhibit the binding of antibodies to FcRs.

Another further subject of the present invention are immunoglobulin inhibitors which have a three-dimensional structure which is complementary to the immunoglobulin binding site for recombinant soluble Fc receptors according to the invention and inhibit the binding of immunoglobulins to Fc receptors.

The term "complementary" is to be understood within the framework of the invention in such a way that the inhibitor molecules must be substances which are able to cover at least so many binding sites on the immunoglobulin or on the Fc receptor that the binding between Fc receptor and immunoglobulin is at least decisively weakened. Covering can take place both by binding to the amino acids mediating the complex formation of either component but also in such a way that at least complex formation is no longer possible, be it by sterically inhibition or by binding to adjacent amino acids, however, covering the amino acid involved in the complex binding between Fc receptor and immunoglobulin.

In connection with the present invention it was possible for the first time to determine the exact binding sites and the amino acids involved in the binding of the antibody and antibody receptor molecules. One is now able to design specifically binding molecules and to screen candidate compositions on the computer. This enables the selection of such compositions from a variety of possibly candidate compositions which can effect a sufficient inhibition of complex formation between Fc receptor and immunoglobulin.

What is important for the inhibitors of the invention is that, owing to their structure and specificity, they are capable of binding to the FcRs or immunoglobulins and thus prevent the normal binding between FcRs and the constant parts of antibodies.

Preferably, such FcR or IgG inhibitors are small organic molecules which can easily be administered orally. They are an interesting alternative to cortisone in the treatment of autoimmune diseases and host/graft rejections. Such a molecule would also suppress reinfection rates with certain viruses, e.g. Dengue virus where the antibody coated virus is FcγRIIb dependent internalized (Littaua et al, 1990), HIV where on CD4 positive T cells an antibody enhancement of HIV infection is mediated by FcγRIII (Homsy at al, 1989), or Ebola where the virus secreted glycoprotein inhibits early neutrophil activation by blocking sFcγRII which affects the host response to infection (Yang at al, 1998).

The development of inhibitors also leads to substances that interfere with the recognition of IgE by their receptors. From the modelled structure of FcεRI, peptides have already been developed which inhibit mast cell degranulation in vitro. With the now available knowledge of the structures of the homologue receptors and the receptor-antibody complex in atomic detail, a new possibility for a rational drug design is opened.

The Fc-receptor bind between the two CH2-domains of the Fc-fragment in the so-called lower hinge region (FIG. 8). The binding region of the Fc-receptor is described in Example 1 (The contact interface to IgG). The residues promoting the interaction between FcR and immunoglobulin are shown in FIGS. 7, 10*a* and 10*b*. Thereby three interaction regions become evident (FIG. 5).

1st Region: FcR (Residues 85 to 87 and Residue 110)-Ig (Chain A Residues 326-328)

Proline 328 of the Ig is clamped by the residues Trp 87 and 110 in a sandwich like manner. These residues are conserved among the IgG and IgE receptors as well as in the IgG and IgE. An inhibitor binding to this prominent region would strongly interfere with binding. This region is additionally attractive for inhibitor design because the exposed hydrophobic surface region comprising the residues Trp 87, Ile 85, Gly 86 of the receptors could be employed to obtain additional binding energy. The functional groups of Thr 113 and Glu 18 and Lys 19 side chains in the vicinity may contribute especially to specific inhibitor binding.

2nd Region: FcR (Residues 126-132 and Residues 155-158)-Ig (Chain A and Chain B Residues 234-239)

The amino terminal residues 234-239 of both Ig chains are recognised differently by the FcR, thereby breaking the 2-fold symmetry of the Fc fragment.

This residues of Fc-fragment chain A are in contact with residues Val 155-Lys 158 of the receptor and the same residues from Fc-fragment chain B with receptor residues Gly 126-His 132. This region shows the most differences in the sequence alignment of the receptors as well as the immunoglobulins and should therefore be involved in specificity generation. This deep cleft between the Fc-fragment chains is well suited for inhibitor design and would be the site of choice for the development of inhibitors when issues of specificity are concerned.

3rd Region: FcR (Residues 117, 126 and 129-132)-Ig (Chain B Residues 264-265 and Residues 296-297)

This binding region is characterised by a clustering of amino acid residues carrying functional groups in their side chains, that might be employed in various ways for inhibitor design on the receptor and the Ig side of the contact.

Molecules that interact with one or more of the above described regions, and are designed or screened explicitly for exploiting the knowledge of binding sites are considered as inhibitors according to the invention.

Further subject matters of the present invention are pharmaceutical compositions containing as active agent an FcR inhibitor or an immunoglobulin inhibitor as mentioned above. Such pharmaceutical compositions may, for example, be used in the treatment or prevention of diseases which are due to overreactions or faulty reactions of the immune system, preferably the treatment or prevention of allergies, autoimmune diseases or anaphylactic shock.

A further subject of the present invention is the sFcR according to the invention, bound to a solid phase. Such heterogeneous receptors can be used for immunoassays or other applications where the receptor in an immobilized form can be used beneficially.

In a preferred embodiment of the invention the solid phase is a chromatography carrier material onto which the Fc receptor is fixed, e.g. sepharose, dextransulfate etc. Such chromatography materials with Fc receptors bound thereto can beneficially be used for the adsorption of immunoglobulins from the blood, plasma or serum of patients or from the culture supernatant of immunoglobulin producing cells (meaning concentration, enrichment and purification of antibodies).

On the one hand, the antibodies bound to the chromatography material can be eluted and, for example, the immune status of a patient can thereby be determined. On the other hand, antibodies from the blood of a patient can thereby be enriched before carrying out further tests, which is a further preferred embodiment of the present invention. In many cases it is difficult to conduct diagnostic assays using blood samples if the latter contains only a very small number of the antibodies to be identified. By means of a concentration using a specific chromatographic column with Fc receptors according to the present invention, antibodies of interest can easily be concentrated and separated from many other substances which might disturb the test.

Basically, it is also possible to use a chromatography material according to the present invention in an extracorporeal perfusion system for lavage of the blood in case of certain diseases where the removal of antibodies plays a crucial role.

It is, however, also possible to use another material as solid phase to which the soluble Fc receptor according to the invention is coupled, e.g. microtiter plates or small reaction vessels to the walls of which Fc receptors are bound either directly or indirectly. Such solid phases and vessels can be particularly important for diagnostic methods, as they enable screening by using immunoassays e.g. for detecting the presence of certain immunoglobins in patients' blood or other body fluids.

To sum up, the recombinant soluble Fc receptors provided by the present invention as well as the corresponding structure determination of crystalline preparations of these receptors and of crystalline complexes of receptors and immunoglobins enable for the first time to perform a rational drug design, wherefrom it is possible to modulate the interaction between immunoglobulins and Fc receptors on cells or soluble receptors. Such a modulation is preferably an inhibition, whereby the inhibition of the formation of a complex from IgG and Fc receptor takes place by covering and preferably by binding of inhibitor molecules to the Fc receptor or the immunoglobulin. There are various medical applications for such modulating drugs and in particular of inhibitors and only few of these applications have been exemplary mentioned within the framework of the present specification. This can and should by no means exclude the applicability of such molecules which have been designed or screened on the basis of the findings about the molecular structure or FcR/Ig complexes disclosed herein for the treatment or prevention of other health disturbances.

The following Examples are to further illustrate the invention in conjunction with the Figures.

EXAMPLE 1 shFcγRIIb (Soluble Human FcγRIIb)

1.1 Cloning and Expression

The cDNA of human FcγRIIb2 (Engelhardt at al, 1990) was modified using mutagenous PCR (Dulau at al, 1989). Therefore, a forward primer was used for the introduction of a new start methionine after the cleavage site of the signal peptide within a NcoI site (5'-AAT AGA ATT CCA TGG GGA CAC CTG CAG CTC CC-3' (SEQ ID NO: 19) while the reverse primer introduced a stop codon between the putative extracellular part and the transmembrane region so followed by a Sa/I site (5' CCC AGT GTC GAC AGC CTA AAT GAT CCC C-3' (SEQ ID NO: 20). The PCR product was digested with NcoI and Sa/I, cloned into a pET11d expression vector (Novagen) and the proposed sequence was confirmed. The final construct was propagated in BL21(DE3) (Grodberg and Dunn, 1988). For the overexpression of FcγRIIb a single colony of the transformed bacteria was inoculated in 5 ml LB medium containing 100 µg ampicillin per ml (LB-Amp100) and incubated overnight at 37° C. The culture was diluted 200-fold in LB-Amp100 and incubation was continued until an OD600 of 0.7-0.9 was achieved. The overproduction of the protein was induced by adding WIG to a final concentration of 1 mM. After a growing period of 4 hours the cells were harvested by centrifugation (30 min, 4000×g) and resuspended in sonification buffer (30 mM sodium phosphate, 300 mM sodium chloride, 0.02% sodium azide, pH 7.8). After addition of 0.1 mg lysozyme per ml suspension and incubation for 30 min at room temperature the sonification was performed on ice (Branson Sonifier, Danbury, Conn.; Macrotip, 90% output, 80% interval, 15 min), The suspension was centrifuged (30 min, 30,000×g) and resuspended with a Dounce homogenizer in sonification buffer containing 0.5% LDAO. The centrifugation step and resuspension in LDAO containing buffer was repeated once before this procedure was repeated twice without LDAO, The purified inclusion bodies were stored at 4° C.

1.2 Refolding and Purification of Soluble Human FcγRIIb (shFcγRIIb) SEQ ID NO: 3

The purified inclusion bodies were dissolved to a protein concentration of 10 mg/ml in 6 M guanidine chloride, 100 mM 2-mercaptoethanol and separated from the insoluble matter by centrifugation. The refolding was achieved by rapid dilution. Therefore, one ml of the inclusion body solution was dropped under stirring within 15 hours into 400 ml of the refolding buffer (0.1 M TRIS/HCl, 1.4 M arginine, 150 mM sodium chloride, 5 mM GSH, 0.5 mM GSSG, 0.1 mM PMSF, 0.02% sodium azide, pH 8.5, 4° C.). Afterwards, the mixture was stirred for 2-3 days until the concentration of free thiol groups was reduced to 1 mM by air oxidation as measured according to Ellman (Ellman, 1959). The solution was dialyzed against PBS and sterile filtered before it was concentrated 10-fold in a stirring cell equipped with a 3kD MWCO ultrafiltration membrane. The protein solution was applied to a hIgG sepharose column (50 mg hIgG per ml sepharose 4B). Unbound protein was washed out with 50 mM TRIS pH 8.0 before elution of FcγRIIb by pH jump (150 mM sodium chloride, 100 mM glycine, 0.02% sodium azide, pH 3.0). The eluate was immediately neutralized with 1 M TRIS pH 8.0. The FcγRIIb containing solution was concentrated and subjected to gel filtration on a Superdex-75 column equilibrated with crystallization buffer (2 mM MOPS 150 mM sodium chloride, 0.02% sodium azide pH 7.0). The fractions containing FcγRIIb were pooled, concentrated to 7 mg/ml and stored at −20°C.

1.3 Equilibrium Gel Filtration Experiments

A Superdex75 column was connected to FPLC and equilibrated with PBS containing 10 µg shFcγRIIb SEQ ID NO:3 per ml. Human Fc fragment was solved to a concentration of 1 µg/10 µl in the equilibration buffer and injected. The resulting chromatogram yielded a positive peak comprising the complex of the shFcγRIIb SEQ ID NO:3 and the Fc fragment while the negative peak represents the lack of receptor consumed from the running buffer for complex formation.

1.4 A Crystallization and Data Collection

Initial crystallization trials employing a 96 condition sparse matrix screen (Jancarik and Kim, 1991) were performed in sitting drops at 20°C using the vapor diffusion method. Occurring crystals were improved by changing the pH as well as the salt, precipitant and additive concentration. Diffraction data from suitable crystals was collected on an image plate system (MAR research) using graphite monochromated CuK$_\alpha$radiation from a RU200b rotating anode generator (Rigaku) operated at 50 kV and 100 mA. The reflections were integrated with the program MOSFLM (Leslie, 1997) and subsequently the data was scaled, reduced and truncated to obtain the structure-factor amplitudes using routines from the CCP4 program suite (Collaborative Computational Project, 1994).

1.5 Summary of Expression, Purification and Refolding of shFcγRIIb (SEQ ID NO:3)

The extracellular part of FcγRIIb was expressed in high levels under the control of a T7 promoter in the T7 RNA polymerase positive E. coli strand BL21/DE3 (Grodberg & Dunn, 1988). The protein was deposited in inclusion bodies, which were employed in the first purification step. The isolation of the inclusion bodies was started with an intense combined lysozyme/sonification procedure to open virtually all cells which would otherwise contaminate the product. The subsequent washing steps with the detergent LDAO, which has excellent properties in solving impurities but not the inclusion bodies itself already yielded a product with a purity of >90% (FIG. 1).

This product was used for refolding trials without further purification. The inclusion bodies were dissolved in high concentration of 2-mercaptoethanol and guanidine to ensure the shift of covalent and non-covalent aggregates to monomers. This solution was rapidly diluted with refolding buffer to minimize contacts between the unfolded protein molecules which would otherwise form aggregates. The use of arginine in the refolding buffer prevents the irreversible modification of side chains as often recognized with urea. After addition of the protein to the refolding buffer, the solution was stirred at 4° C. until the concentration of free thiol groups was reduced to 1 mM, which was absolutely necessary as earlier dialysis resulted in an inactive product. In a second purification step the dialyzed and refolded FcγRIIb was bound to immobilized hIgG to remove minor fractions of E. coli proteins and inactive receptor. The protein was eluted with a pH jump and immediately neutralized. After this affinity chromatography step shFcγRIIb is essentially pure except for a minor contamination resulting from the coeluting IgG which leached out of the matrix even after repeated use (FIG. 1). The IgG as well as receptor multimers which are not visible in the reducing SDS-PAGE could easily be removed by gel filtration. Parallel to the removal of the contaminants in this step the buffer is quantitatively exchanged. This procedure ensures a defined composition of the protein solution as even slight variations can cause irreproducibility of the crystallization attempts or even inhibit the formation of crystals. Overall 6 mg pure protein could be gained per litre E. coli culture, which is about 10% from the FcγRIIb content of the inclusion bodies.

N-terminal protein sequencing revealed the identity with the expected sequence $H_2N$-GTPAAP (SEQ ID NO: 21) without detectable contamination, ESI-MS analysis showed that the final material used in crystallization trials is homogenous with respect to size. From the primary sequence the molecular weight was calculated to 20434 Da, which corresponds to 20429 Da found by mass spectroscopy. The discrepancy lies within the error of the instrument, and no additional peak for a species containing the leading methionine is found.

The crystallization of shFcγRIIb (SEQ ID NO: 3) was performed in sitting drops using the vapor diffusion method. Initial trials with a sparse matrix screen (Jancarik & Kim, 1991) resulted already in small crystalline needles. Subsequent optimization of the preliminary crystallization condition by varying precipitant, salt, their concentration and pH led to the isolation of three different crystal forms. Orthorhombic crystals grew from mixture of 1.5 µl reservoir solution (33% PEG2000, 0.2 M sodium acetate, pH 5.4) with 3 µl of the protein solution. They appeared within 3 days and reached their final size of approximately 80 µm x 80 µm x 500µm after one week. These crystals diffracted to 1.7 Å. Crystals could also he grown in two other space groups from reservoir solution containing 26% PEG8000, 0.2 M sodium acetate, pH 5.6, 5 mM $Zn(OAc)_2$, 100 mM sodium chloride (hexagonal form) and 26% PEG8000, 0,2 M NaOAc, pH 5.6, 10% (v/v) 1,4-Dioxan, 100 mM sodium chloride (tetragonal form). These crystals were of suitable size for X-ray analysis but diffracted only to 2.7Å and 3.8 Å for the tetragonal and hexagonal crystal form respectively (Table 1).

FcγRII was expressed in E. coli which, besides the comparatively low production costs and the availability, has several advantages especially when the glycosylation performed by mammalian cells is not necessary for the function of the protein as in the case of FcγRII where IgG binding occurs independently of carbohydrate attachment (Sondermann at al, 1998A). In E. coli a homogenous product can reproducibly be generated, which is in contrast to the expression in mammalian cells where batch dependent variances are often observed. In such a system the product is for several days exposed to proteases at temperatures of more than 30° C. in contrary, the expression of the protein in E. coli under the control of the strong T7 promoter at 37° C. frequently leads to the formation of protease inaccessible inclusion bodies. A further advantage of the expression in bacteria is that the material could be considered to be free of pathogenic germs, which might derive from employed fetal calf serum or the cell line itself. In mammalian expression particular care must be taken during the purification of the target protein because potential effective hormones or growth factors might be copurified. One case where the effects of sFcγR were ascribed to a TGFβ1 contamination is already reported (Galon at al, 1995).

1.6 Purification

The purification procedure is straightforward. It consists of three steps which can easily be performed in a single day. The protein is obtained in a pure form and in high yields and could even be obtained in considerable quality without the expensive IgG affinity column. The success of such a protocol would depend on the careful preparation of the inclusion bodies, as most of the impurities can be eliminated already in the first purification step.

1.7 Characterization

The purified FcγRIIb was characterized by SOS-PAGE and isoelectric focussing as well as N-terminal sequencing and mass spectroscopy. Thus, the material can be considered pure and homogeneous with respect to its chemical composition, but the intriguing question whether the receptor is correctly folded remains to be discussed. All cysteins are paired, since no free thiol groups are detected with Ellman's test. The material is monomeric and eludes with the expected retention time in peaks of symmetrical shape from a size exclusion chromatography column. Furthermore, FcγRIIb binds to IgG sepharose, recombinant FcγRIIb from E. coli is active because it specifically binds IgG.

1.8 Crystallization

The orthorhombic crystal form of FcγRIIb diffracted X-rays to a resolution of 1.7 Å, which is a drastic improvement compared to previously reported crystals of the same molecule derived from insect cell expression (Sondermann at al, 1998A). These crystals diffracted to 2.9 Å and were of space group $P3_121$. Thus, the glycosylation of the insect cell derived receptor influences the crystallization conditions. Instead of the trigonal space group, three different crystal forms are found. After a possible solution of the structure these crystal forms will help identify artificial conformations of the protein due to crystal contacts.

FcγRs do not exhibit any sequence similarity to other proteins but due to a conserved cystein spacing they are affiliated to the immunoglobulin super family. Consequently, we tried to solve its structure by molecular replacement, but extensive trials using IgG domains from a variety of molecules failed.

Thus the structure of FcγRIIb has to be solved by the methods of multiple isomorphous replacement.

We have shown for the first time that FcγRIIb can be obtained in an active form from *E. coli*. This is the basis for crystallographic investigations that will soon, due to the already gained crystals of exceptional quality, result in the structure solution of this important molecule. The structure will provide information on the IgG binding site and provide a starting point for the knowledge based design of drugs that interfere with recognition of the ligand by its receptor. Furthermore, because of the high homology between FcγRIIb and other FcRs including FcεRIa it seems possible that these molecules can be produced in the same way, which would provide valuable material for the ongoing research.

1.9 Methods

Protein Chemistry

Recombinant soluble human FcγRIIb was expressed in *E. coli*, refolded purified and crystallized as described elsewhere (Sondermann at al, 1998B). Briefly, the putative extracellular region of hFcγRIIb2 (Engelhardt at al, 1990) was overexpressed in *E. coli*. Inclusion bodies were purified by lysozyme treatment of the cells and subsequent sonification. The resulting suspension was centrifuged (30 min 30,000×g) and washed with buffer containing 0.5% LDAO. A centrifugation step and resuspension in LDAO containing buffer was repeated once before this procedure was repeated twice without LDAO. The inclusion bodies were solved in 6 M guanidine hydrochloride and the protein was renaturated as described. The dialyzed and filtrated protein solution was applied to a hIgG sepharose column and eluted by pH jump. The concentrated neutralized fractions were subjected to size-exclusion chromatography on a Superdex-75 column (26/60, Pharmacia).

Crystallization

Crystallization was performed in sitting drops at 20° C. using the vapor diffusion technique. Crystallization screens were performed by changing pH, salt, precipitant and additives. The final crystals used for data collection were grown in 33% PEG2000, 0.2 M sodium acetate, pH 5.4 (orthorhombic form) 26% PEG8000, 0.2 M sodium acetate, pH 5.6, 10% (v/v) 1,4-dioxane, 100 mM sodium chloride (tetragonal form), and 26% PEG8000, 0.2 M sodium acetate, pH 5.6, 5 mM ZN(OAc)$_2$, 100 mM sodium chloride (hexagonal form). The insect cell derived protein was crystallized in 32% PEG6000, 0.2 M sodium acetate, pH 5.3.

Preparation of Heavy-Atom Derivatives

The heavy-atom derivatives were prepared by soaking the crystals in the crystallization buffer containing 2 mM platinum(II)-(2,2'-6,2''terpyridinium) chloride for 24 hours or 10 mM uranylchloride for 8 days.

X-Ray Data Collection

Diffraction Data was Collected on an Image Plate System (MAR Research) using graphite monochromated CuK$_α$ radiation from a RU200b rotating anode generator (Rigaku) operated at 50 kV and 100 mA. The reflections were integrated with the program MOSFLM 5.50 (Leslie, 1997) and subsequently the data was scaled and truncated to obtain the structure-factor amplitudes using routines from the CCP4 program suite (Collaborative Computational Project, 1994).

Structure Determination

The structure was solved with the standard procedures of the MIR method. From the large number of soaks carried out with different heavy-atom components only the two compounds yielded interpretable Patterson maps. The heavy-atom positions for each derivative were determined from difference Patterson maps and initial phases were calculated. Cross-phased difference Fourier maps were used to confirm heavy atom positions and establish a common origin for the derivatives. Anomalous data were included to discriminate between the enantiomers. The heavy atom parameters were further refined with the program MLPHARE from the CCP4 package leading to the statistics compiled in Table 2. An electron-density map was calculated to a resolution of 2.1 Å and the phases were improved further by solvent flattening and histogram matching with the program DM from the CCP4 suite. The resulting electron density map was of sufficient quality to build most of the amino acid residues. Model building was performed with O (Jones at al, 1991) on an Indigo2 work station (Silicon Graphics Incorporation). The structure refinement was done with XPLOR (Brünger at al, 1987) by gradually increasing the resolution to 1.7 Å using the parameter set of Engh and Huber (Engh & Huber, 1991). When the structure was complete after several rounds of model building and individual restraint B-factors refinement ($R_{fac}$=29%/$R_{Free}$=36%), 150 water molecules were built into the electron density when a Fo-Fc map contoured at 3.5 σ coincided with well defined electron density of a 2Fo-Fc map contoured at 1 σ. The resulting refinement statistic is shown in Table 3.

1.10 Structure Determination

The crystal structure of recombinant soluble human FcγRIIb was solved by multiple isomorphous replacement (MIR) to 1.7 Å resolution, since a structure solution by molecular replacement with isolated domains of the Fc fragment from human IgG1 (Huber et al, 1976, PDB entry 1fc1; Deisenhofer, 1981) failed. The putative extracellular part of the receptor (amino acid residues 1-187 as depicted in SEQ ID NO: 3) was used for crystallization trials (Sondermann et al, 1998B) while the model contains the residues 5-176 as the termini are flexible and not traceable into the electron density. Additionally, the model contains 150 water molecules and the refinement statistics are summarized in Table 2. The structure contains a cis proline at position 11. None of the main chain torsion angles is located in disallowed regions of the Ramachandran plot. The fully refined model was used to solve the structure of the same protein in crystals of space group P4$_2$2$_1$2 and of the glycosylated form derived from insect cells in crystals of space group P3$_1$2$_1$ (Table 2).

The polypeptide chain of FcγRIIb folds into two Ig-like domains as expected from its affiliation with the immunoglobulin super family. Each domain consists of two beta sheets that are arranged in a sandwich with the conserved disulfide bridge connecting strands B and F on the opposing sheets (FIG. 3). Three anti-parallel β-strands (A1, B, E) oppose a sheet of 5 β-strands (C', C, F, G, A2), whereby strand A1 leaves the 3-stranded β-sheet and crosses over to the 4-stranded anti-parallel sheet adding the short parallel 5th strand A2. The arrangement of secondary structure elements as well as their connectivity is identical in both domains of the FcγRIIb and a rigid body fit of one domain onto the other revealed a r.m.s. distance of 1.29 Å of 67 matching Cα atoms.

The domains are arranged nearly perpendicularly to each other enclosing an angle of 70 degrees between their long axes forming a heart-shaped overall structure. This arrangement results in an extensive contact region between the domains (FIG. 4). Residues from strand A2 and from the segment linking A2 and A1 of the N-terminal domain intermesh with residues of strands A1 and B from the C-terminal domain. This region is tightly packed and the interaction is strengthened by several hydrogen bonds resulting in a rigid arrangement. This is confirmed by the conservation of the structure in three different space groups. In orthorhombic, tetragonal and hexagonal (insect cell derived) crystal forms a deviation of less than 2° in the interdomain angle is found.

1.11 Overall Structures

The structure of recombinant human FcγRIIb derived from *E. coli* was solved by MIR to 1.7 Å resolution from orthorhombic crystals. An essentially identical structure is found in tetragonal and with protein derived from insect cells in hexagonal crystals. In all three structures the last nine residues of the polypeptide chain were found disordered. The flexibility of the C-terminal linker region between the structured core of the molecule and the transmembrane part may be functionally relevant to allow some reorientation of the receptor to enhance the recognition of the Fc parts in immunocomplexes.

1.12 Homologue Receptors

The Ig domains found in the Ig super family of proteins are characterized by a beta sandwich structure with a conserved disulfide bridge connecting two strands of the opposing sheets. The typical arrangement of 3 and 4 anti parallel beta strands that form a sandwich as found in FcγRIIb occurs also in the T cell receptor, Fc fragment, CD4 or the Fab fragment. A structural alignment of the individual Ig domains of these molecules with the two domains of FcγRIIb shows a common, closely related structure. The relative arrangement of the domains, however, is not related in these molecules and covers a broad sector. Despite the structural similarity between Ig domains from different molecules and the strikingly low r.m.s. deviation of Cα atoms that result when the two domains of FcγRII are superimposed, no significant sequence similarity is found (FIGS. 5a and 5b). A structure-based sequence alignment shows a conserved hydrophobicity pattern along the sequence of the domains, together with, beside the cysteines, only few identical amino acid residues. We first prepared a structure-based alignment of the two C-terminal domains of the IgG1 heavy chain and the FcγRIIb and added the sequences of the other related FcγR and the FcεRIa domains. This shows that the sequences of the three domain FcγRI and the two domain receptors are compatible with the hydrophobicity pattern of Ig domains and several conserved amino acid residues are revealed. Firstly, the different domains of an FcR are more related to each other than to Ig domains from other molecules of the Ig super family. Secondly, the N-terminal domains of the receptors relate to each other as the second domains do. Thirdly, the sequence of the third domain of FcγRI shows features from both groups of domains. Taken together, we confirm the affiliation of the FcRs to the Ig super family and speculate that all FcR-domains originate from a common ancestor, an ancient one domain receptor that acquired a second domain by gene duplication. Further divergent development of such a two domain receptor resulted in the present diversity, including FcγRI that acquired a third domain.

Conservation of these amino acid residues that contribute to the interdomain contact in FcγRIIb in the alignment are a hint to a similar domain arrangement in different receptors. In Table 4 the residues contributing with their side chains to the interdomain contact (FIG. 4) are compiled for FcγRIIb together with the corresponding amino acid residues in other receptors according to the structure-based sequence alignment of FIG. 5b. Except for Asn15, which is not conserved between the FcRs, the involved residues are identical or conservatively replaced providing strong support for a similar structure and domain arrangement in all FcRs.

1.13 The Contact Interface to IgG

Limited information about the interactions of FcRs with their ligands is available from mutagenesis studies (Hogarth et al, 1992; Hulett at al, 1994; Hulett at al, 1995). By systematically exchanging loops between the β-strands of FcγRIIa for FcεRIa amino, acid residues the B/C, C'/E and F/G loops of the C-terminal domain were evaluated as important for ligand binding (FIG. 3, FIG. 5b). In the structure model these loops are adjacent and freely accessible to the potential ligand. Additionally, most of the amino acid residues in these loops were exchanged for alanines by single site mutations which resulted in a drastic alteration of the affinity of FcγRIIa to dimeric human IgG1. Also, the single amino acid exchange Arg 131 to His in the C-terminal domain (C'/E loop) in the high responder/low responder polymorphism, which alters the affinity of the FcγRIIa to murine IgG1, points to that region. Thus, the amino acid residues in this area are either important for ligand binding or the structural integrity of that region. Here, the structure shows a clustering of the hydrophobic amino acid residues Pro 114, Leu 115 and Val 116 in the neighbourhood of Tyr 157. This patch is separated from the region Leu 159, Phe 121 and Phe 129 by the positively charged amino acid residues Arg 131 and Lys 117 which protrude from the core structure (FIG. 5b).

1.14 Glycosylation

In the sequence of FcγRIIb three potential N-glycosylation sites are found. All three sites are on the surface of the molecule and are accessible. They are located in the E/F loops (N61 and N142) of both domains and on strand E (N135) of the C-terminal domain (FIG. 3, FIG. 6). Since the material used for the solution of this structure was obtained from *E. coli*, it does not contain carbohydrates, while the FcRs isolated from mammalian cells are highly glycosylated. The three potential glycosylation sites are located rather far from the putative IgG binding region, and non-glycosylated FcγRIIb binds human IgG, suggesting a minor role of glycosylation in binding. This was confirmed by the structure of the FcγRIIb produced in insect cells which is glycosylated (Sondermann et al, 1998A). Except for a 2° change of the interdomain angle possibly due to different crystal contacts, no differences between the glycosylated and unglycosylated protein structures were found. The three glycosylation sites are only optionally used as shown by SDS-PAGE where the material appears in 4 bands. No additional electron density for those sugars was found a consequence of chemical and structural heterogeneity.

EXAMPLE 2 shFcγRIIa (Soluble Human FcγRIIa) SEQ ID NO:2

The procedures were performed according to example 1 except for the indicated changes:

2.1 Cloning and Expression shFcγRIIa SEQ ID NO:2 was generated by mutating the respective wild-type cDNA (Stengelin at al., 1988) and expressed according to example 1 with the mutagenous primers listed in table 5. For the expression of the protein a pET22b+ vector was chosen.

2.2 Refolding and Purification shFcγRIIa SEQ ID NO:2 was refolded according to example 1 with the respective refolding buffer listed in table 6.

2.3 Crystallisation shFcγRIIa SEQ ID NO:2 was crystallised as described under conditions indicated in table 7.

2.4 Structure Determination

The structure was solved with the method of isomorphous replacement with shFcγRIIb as search model.

EXAMPLE 3 shFcγRIII (Soluble Human FcγRIII) SEQ ID NO:4

The procedure was performed according to example 1 except for the indicated changes:

3.1 Cloning and Expression shFcγRIII SEQ ID NO:4 was generated by mutating the respective wild-type cDNA (Simmons & Seed, 1988) and expressed according to example 1 with the mutagenous primers listed in table 5. For the expression of the protein a pET22b+ vector was chosen.

3.2 Refolding and Purification shFcγRIII SEQ ID NO:4 was refolded according to example 1 with the respective refolding buffer listed in table 6.

3.3 Crystallisation shFcγRII was crystallised as described under conditions indicated in table 7.

3.4 Structure Determination

The structure was solved with the method of isomorphous replacement with shFcγRIIb SEQ ID NO:3 as search model.

3.5 Crystallisation of a shFcγRIII(SEQ ID NO:4):hFc1 Complex hIgG1 derived from the serum of a myeloma patient was used to prepare Fc-fragments (hFc1) by digestion with plasmin (Deisenhofer at al., 1976). The resulting Fc-fragments were separated from the Fab-fragments by protein A chromatography. Partially digested hIgG was Removed by size exclusion chromatography with MBS (2 mM MOPS, 150 mM NaCl, 0.02% sodium azide, pH 7.0) as running buffer. Equimolar amounts of hFc1 and shFcgRIII were mixed and diluted with MBS to a concentration of 10 mg/ml. The complex was crystallized as described under conditions indicated in table 7.

EXAMPLE 4 shFcεRII (Soluble Human FcεRII) SEQ ID NO:6

The procedure was performed according to example 1 except for the indicated changes:

4.1 Cloning and Expression

FcεRII was generated by mutating the respective wild-type cDNA (Kikutani at al., 1986) and expressed according to example 2 with the mutagenous primers listed in table 5. For the expression of the protein a pET23a+ vector was chosen.

4.2 Refolding and Purification 4.2 Refolding and Purification Refolding of shFcεRII SEQ ID NO:6 was achieved as described in example 1, with the exception that prior to rapid dilution the dissolved inclusion bodies were dialysed against 6M guanidine chloride, 20 mM sodium acetate, pH 4.0. shFcεRII SEQ ID NO:6 was refolded according to example 1 with the respective refolding buffer listed in table 6. After refolding the protein solution was dialysed against PBS, concentrated 100-fold and purified by gel filtration chromatography on Superdex 75. This yielded pure shFcεRII SEQ ID NO:6 which was dialysed against 2 mM TRIS/HCl, 150 mM NaCl, 0.02% sodium azide, pH 8.0, concentrated to 10 mg/ml and stored at 4° C.

EXAMPLE 5 shFcγRI (Soluble Human FcγRI) SEQ ID NO:1

The procedure was performed according to example 1 except for the indicated changes:

5.1 Cloning and Expression shFcγRI SEQ ID NO:1 was generated by mutating the respective wild-type cDNA (Allen & Seed, 1988) and expressed according to example 1 with the mutagenous primers listed in table 5. For the expression of the protein a pET32a+ vector was chosen, which contains after the N-terminal thioredoxin a hexahistidine-tag with a C-terminal thrombin cleavage site followed by, the shFcγRI SEQ ID NO:1 in frame with the mentioned proteins and amino acid residues. For the overexpression of the fusion protein the $E.$ $coli$ strain BL21(DE3) containing the plasmids pUBS and pLysS (Novagen) was used.

The purified inclusion bodies were solubilised in 6M guanidine-HCl, 10 mM β-mercaptoethanol, 50 mM Tris pH8.0 and bound to a Ni-NTA column (Qiagen). The elution was performed with an imidazole gradient ranging from 0 to 1M imidazole. The eluted protein was dialysed against a 1000 fold volume of 150 mM NaCl, 50 mM Tris pH8.0, 2 mM GSH, 0.5 mM GSSG for 24 hours at 4° C. After concentrating the protein solution to 25% of the initial volume, thrombin was added. After 6 h of incubation at 37° C. the N-terminal thioredoxin and the His-tag were removed completely as verified by N-terminal sequencing. During this digestion the shFcgRI precipitated quantitatively out of solution.

5.2 Refolding and Purification shFcγRI SEQ ID NO:1 was refolded according to example 1 with the respective rethlding buffer listed in table 6. After the redox potential decresased to 1 mM the solution was dialysed against PBS pH8.0 and concentrated.

The refolded Protein was analysed by size exclusion chromatography, which yielded a peak of the proposed monomeric receptor and non reducing SDS-PAGE which showed a major band at 30 kDa.

EXAMPLE 6 shFcγRIa (Soluble Human shFcεRIa) SEQ ID NO:5

The procedure was performed according to example 1 except for the indicated changes:

6.1 Cloning and Expression shFcεRIa SEQ ID NO:5 was generated by mutating the respective wild-type cDNA (Kochan et al., 1988) and expressed according to example 1 with the mutagenous primers listed in table 5. For the expression of the protein a peT23a+ vector was chosen.

1 μg hFc solved in 10 μl equilibration buffer (10 μg sFcγRIIb SEQ ID NO:3 /ml PBS) was applied to a size exclusion chromatography column and the absorbance of the effluent was measured (280 mn) as a function of time. The injected Fc fragment forms a complex with the sFcγRIIb SEQ ID NO:3 in the equilibration buffer (t=22 min), The negative peak of consumed sFcγRIIb SEQ ID NO:3 is observed at t-26 min.

Figure 1:
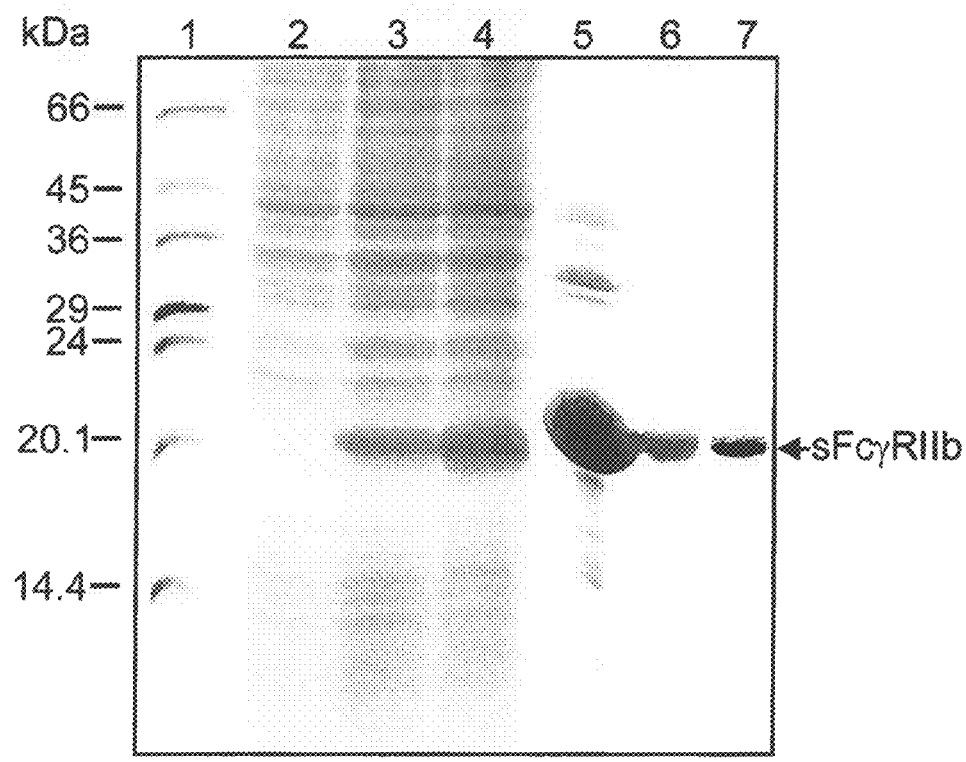
FIG. 1: 15% reducing SDS PAGE showing the purification sFcγRIIb SEQ ID NO:3 Lane 1: Molecular weight marker. Lane 2: $E.$ $coli$ lysate before induction. Lane 3: $E.$ $coli$ lysate 1 h after induction. Lane 4: $E.$ $coli$ lysate 4 h after induction. Lane 5: Purified inclusion bodies of sFcγRIIb SEQ ID NO:3, Lane 6: Eluate of the hIgG affinity column. Lane 7: Pooled fractions of the gel filtration column.
Figure 2:
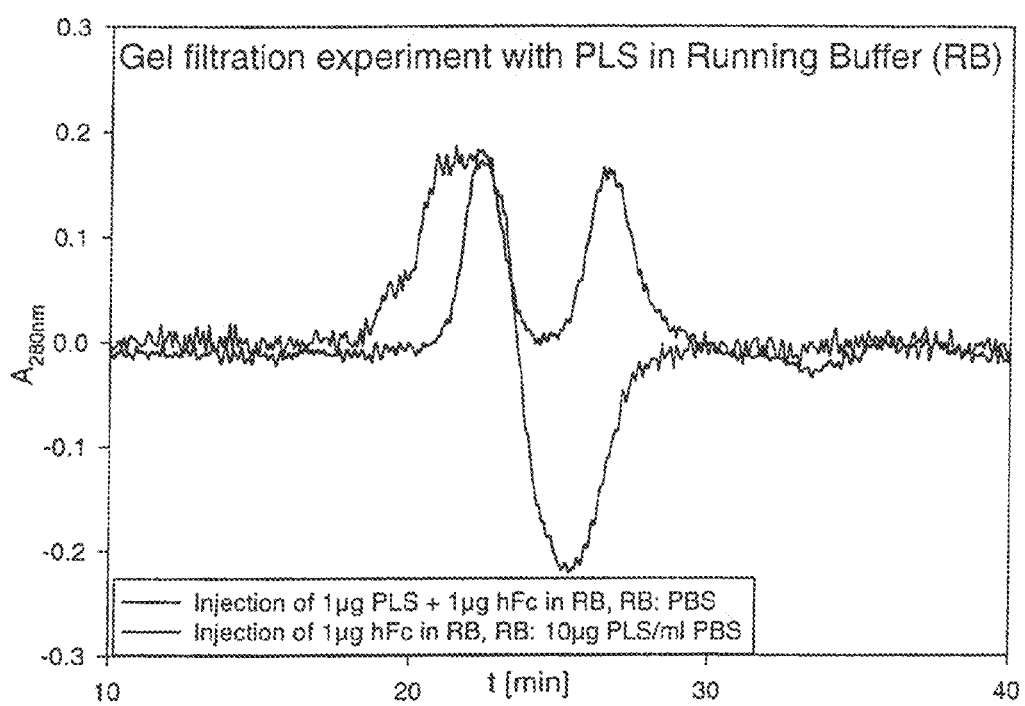
FIG. 2: Equilibrium gel filtration
Figure 3:
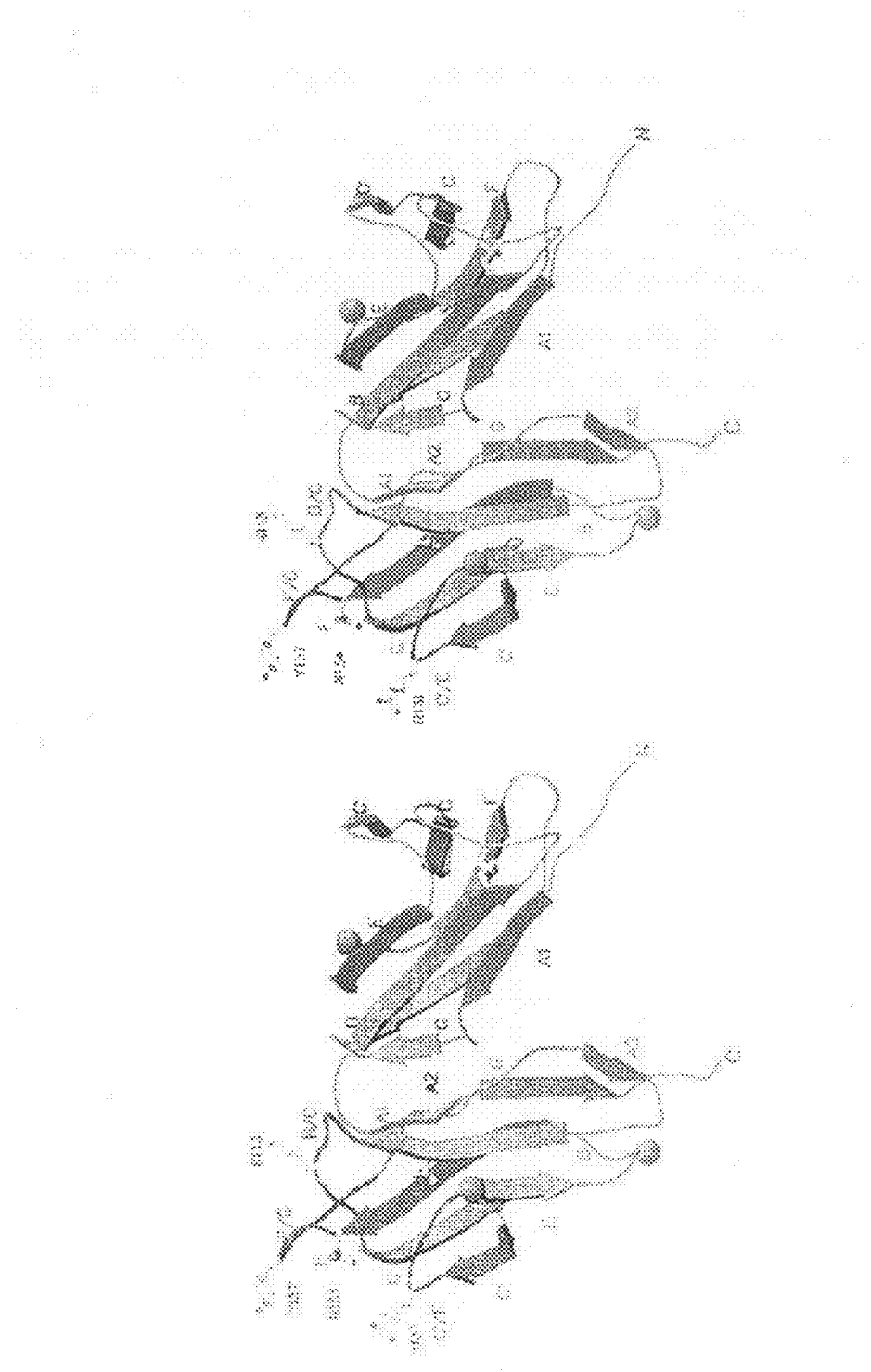

FIG. 3: Overall structure of human sFcγRIIb SEQ ID NO:3

Stereo ribbon representation of the sFcγRIIb SEQ ID NO:3 structure. The loops supposed to be important for IgG binding are depicted in red with some of the residues within the binding site and the conserved disulfide bridge in ball and stick representation. The potential N-glycosylation sites are shown as green balls. The termini are labeled and the β-strands are numbered consecutively for the N-terminal domain in black and for the C-terminal domain in blue. The figure was created using the programs MOLSCRIPT (Kraulis, 1991) and RENDER (Merritt and Murphy, 1994).

Figure 4:
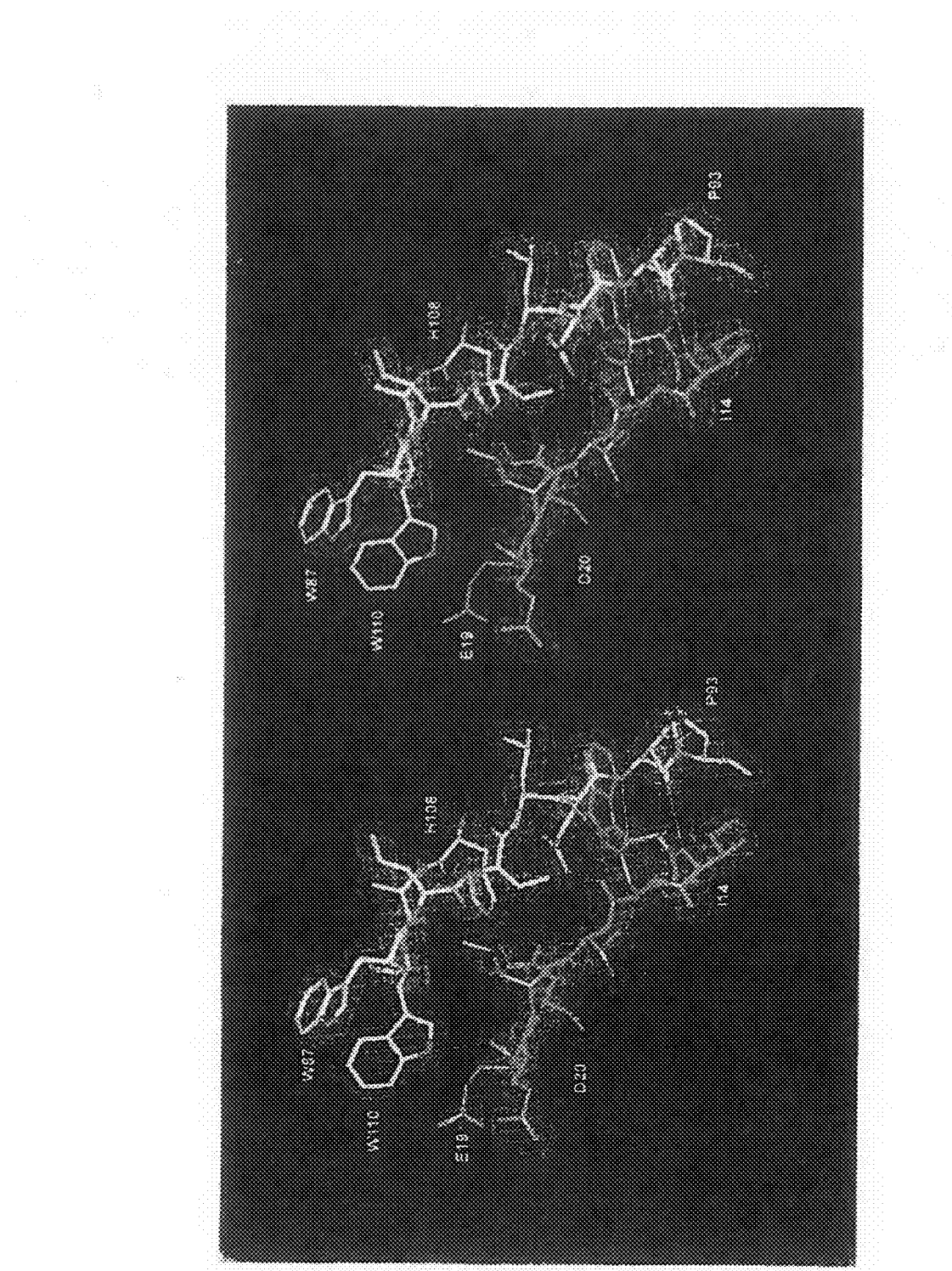

FIG. 4: interdomain contacts

The figure shows a close-up on the residues involved in the interdomain contacts of sFcγRIIb SEQ ID NO:3. The amino acid residues of the N-terminal domain are depicted blue and the residues of the C-terminal domain yellow, The model is covered by a 2Fo-Fc electron density contoured at 1 σ obtained from the final coordinates. Hydrogen bridges between the domains are represented by white lines. The figure was created using the program MAIN (Turk, 1992).

Figure 5A:
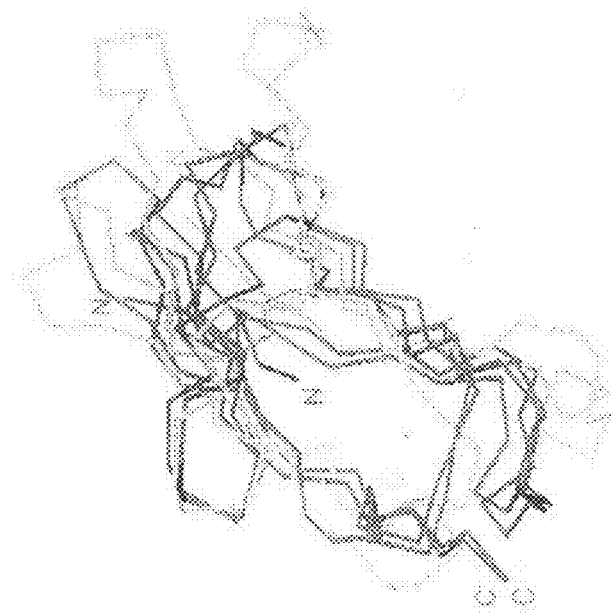
Figure 5A:
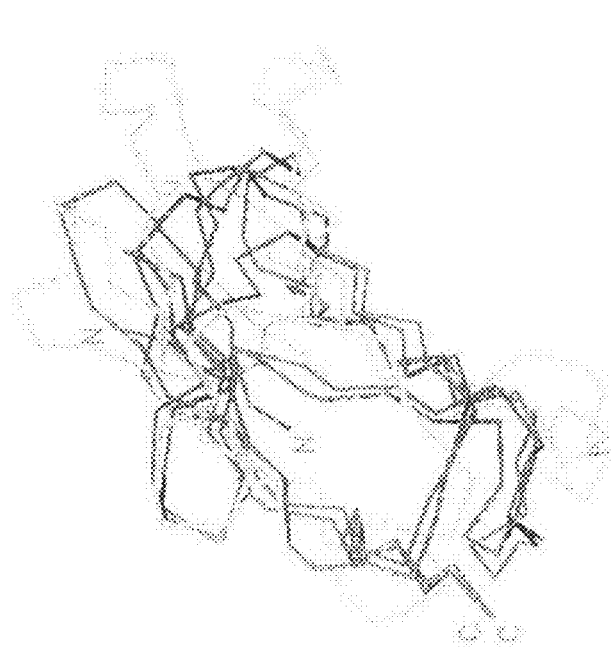

FIG. 5a: Superposition of the two FCγRIIb domains in complex with the CH2 Domain of human IgG1.

Both domains of FcγRIIb were superimposed and complexed with the CH2 domain of hIgG1. The N-terminal domain is depicted in blue, the C-terminal domain in red and the CH2 domain of hIgG1 in green. The respective termini are labeled and the conserved disulfide bridges are depicted as thin lines.

Figure 5B:
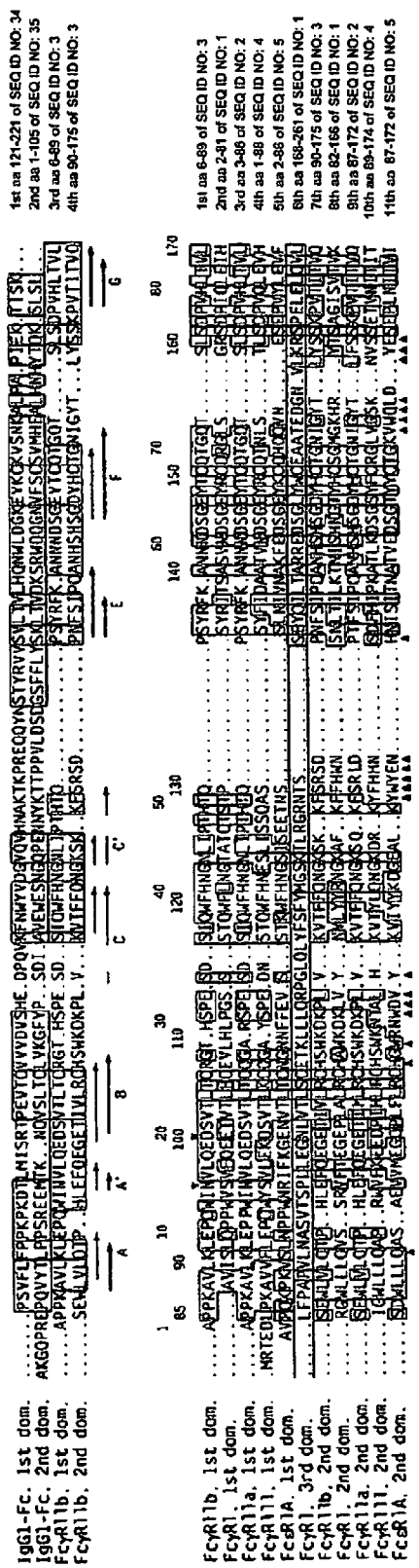

FIG. 5b: Structure based sequence alignment of the sFcγRIIb SEQ ID NO:3 domains with domains of other members of the FcR family The upper part of the figure shows the structure based sequence alignment of IgG1-Fc $1^{st}$ domain SEQ ID NO: 34 (aa 121-221), IgG1-Fc $2^{nd}$ domain SEQ ID NO:35 (aa 1-105), FcγRIIb $1^{st}$ domain SEQ ID NO. 3 (aa 6-89), and FcγRIIb $2^{nd}$ domain SEQ ID NO. 3 (aa 90-175), from top to bottom, performed with the program GBF-3D-FIT (Lessel & Schomburg, 1994). Amino acid residues with a Cα distance of less than 2.0 Å in the superimposed domains are masked: lilac for matching residues between the Fc fragment domains; yellow for residues in the FcγRIIb domains; and green when they can be superimposed in all four domains. The β-strands are indicated below this part of the alignment and are labeled consistent with FIG. 3.

The lower part of the figure shows the alignment of the amino acid sequences of FcγRIIb $1^{st}$ domain SEQ ID NO: 3 (aa 6-89), FcγRI $1^{st}$ domain SEQ ID NO: 1 (aa2-81), FcγRIIa $1^{st}$ SEQ ID NO:2 (aa 3-86), FcγRIII $1^{st}$ domain SEQ ID NO:4 (aa1-88), FcεRIa $1^{st}$ domain SEQ ID NO:5 (aa 2-86), FcγRI $3^{rd}$ domain SEQ ID NO:1 (aa 168-261), FcγγIIb $2^{nd}$ domain SEQ ID NO:3 (aa 90-175), FcγRI $2^{nd}$ domain SEQ ID NO:1 (aa 82-166), FcγRIIa $2^{nd}$ domain SEQ ID NO:2 (aa 87-172), FcγRIII $2^{nd}$ domain SEQ ID NO:4 (aa 89-174), and FcεRIa $2^{nd}$ domain SEQ ID NO:5 (aa 87-172), from top to bottom, to the profile given in the upper part of the figure using routines from the GCG package (Genetics Computer Group, 1994). The upper and lower row of numbering refer to the N- and C-terminal domains of FcγRIIb. The conserved cysteines are typed in magenta and the potential glycosylation sites in blue. Identical residues within the first domain are masked orange, those in the second domain pink and green when the residues are conserved within both domains. The less conserved third domain of FcγRI is aligned between the first and the second domains. Red arrows point to residues that are involved in side chain contacts between the first and the second domain while blue arrows depict residues that are relevant for IgG binding. The figure was produced with the program ALSCRIPT (Barton, 1993).

Figure 6:
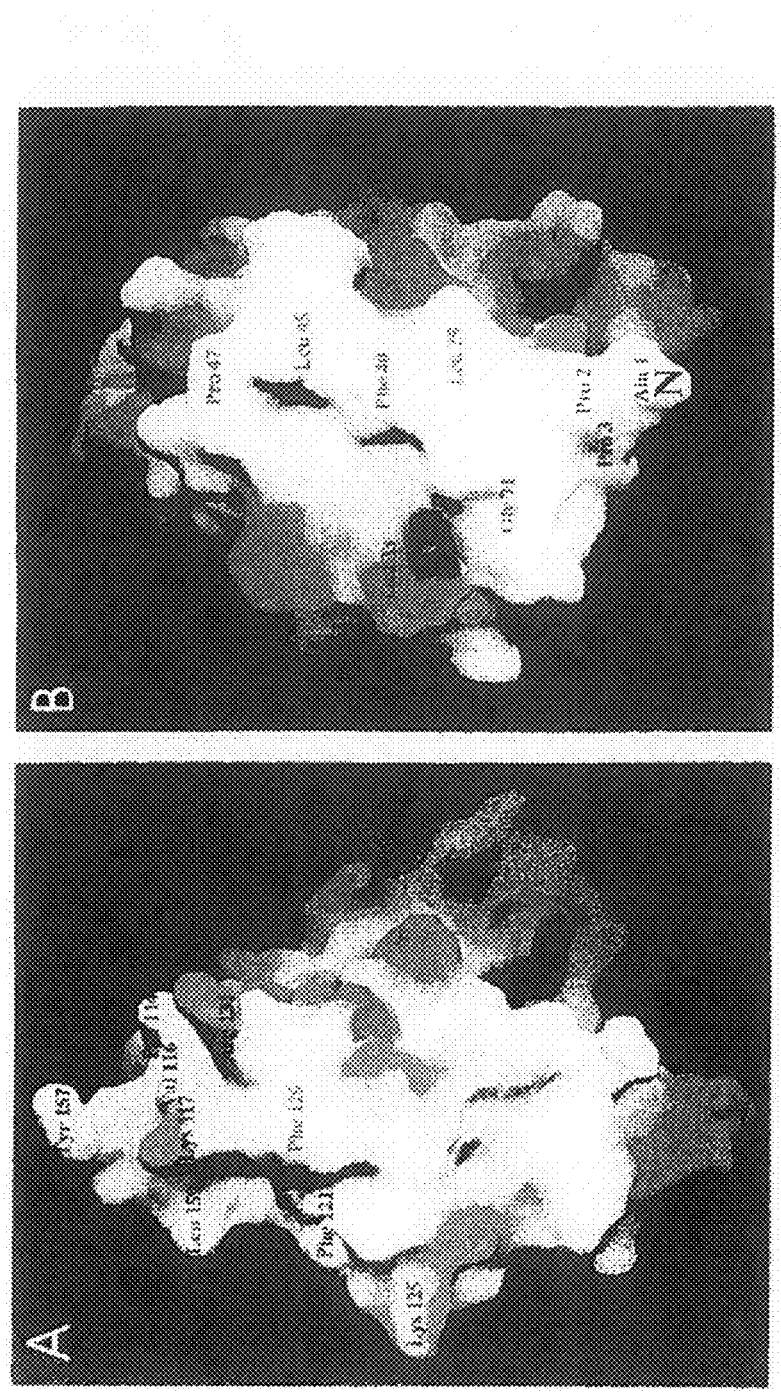

FIG. 6: The putative binding sites of FcγRIIb

Solid surface representations of FcγRIIb as produced with GRASP (Nicholls et al, 1991), the color coding is according to the relative surface potential from negative (red) to positive (blue). FIG. 6a shows the molecule as in FIG. 3 by a rotation of about 90° counter-clockwise around the vertical. In FIG. 6b the molecule is rotated 90° clockwise around the same axis. Both views show the putative binding regions on the C-terminal (FIG. 6a) and the N-terminal domain (FIG. 6b). The amino acid residues discussed in the text are labeled.

Figure 7:
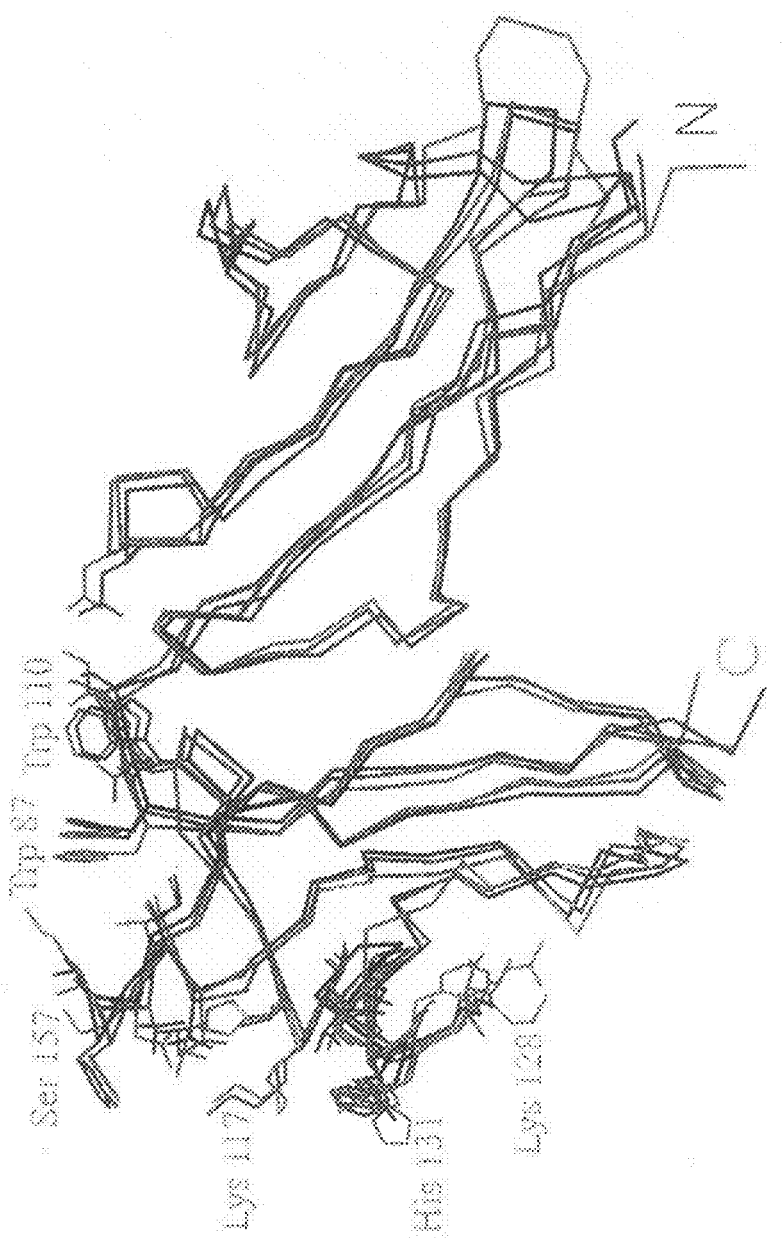

FIG. 7: Cα-trace of the superpositioned structures of the Fcγ-receptors FcγRII red, FcγRIIa green and FcγRIIb blue. Residues important for IgG binding are shown in ball-and-stick. The N- and C-termini are labelled.

Figure 8:
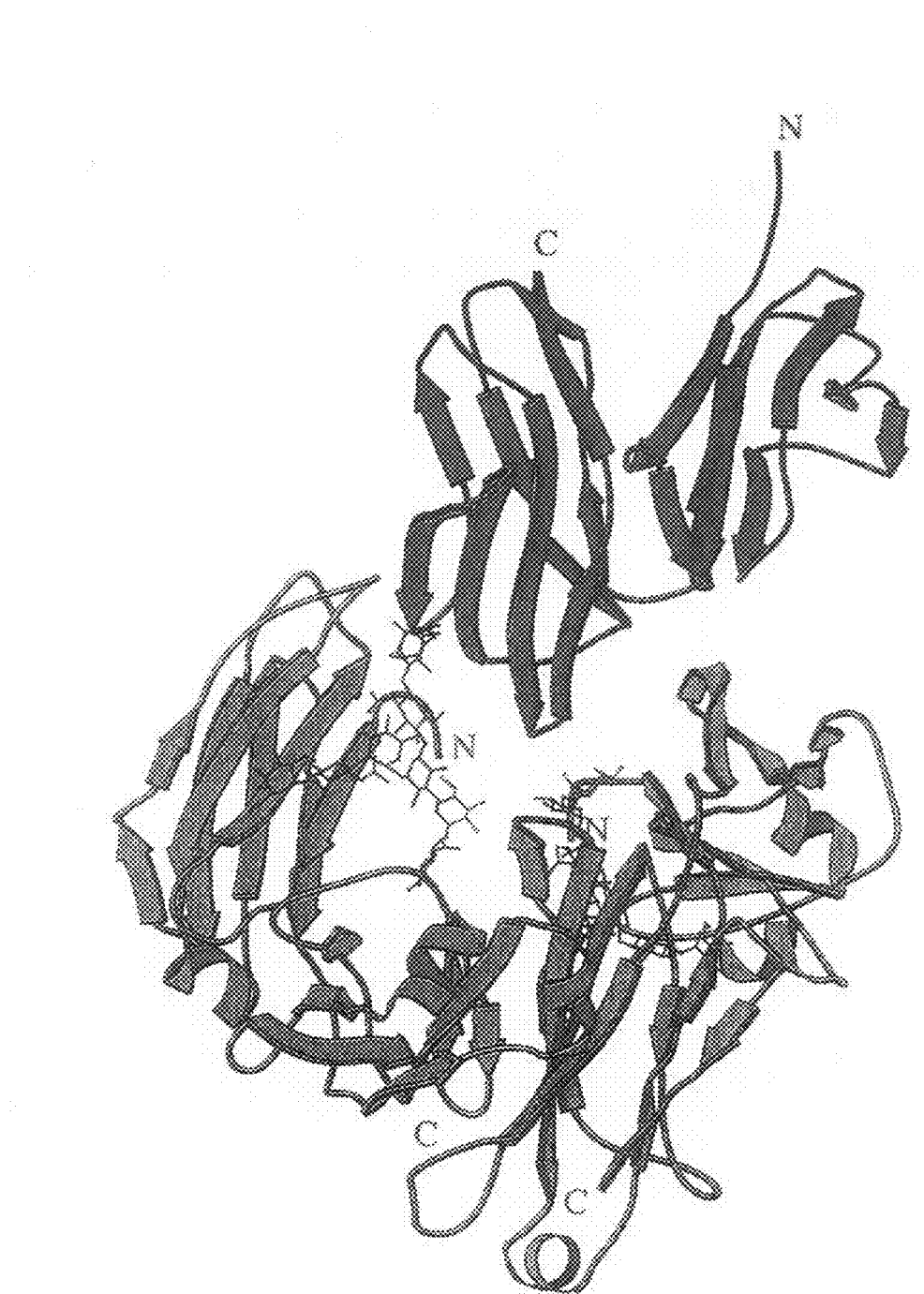

FIG. 8: Overview of the FcγRIII/Fc-fragment crystal structure in ribbon representation The sugar residues bound to the Fc-Fragment are indicated in ball-and-stick. The FcγRII (blue) binds in the lower hinge region between chain-B (red) and chain-A (green) of the Fc-fragment.

Figure 9:
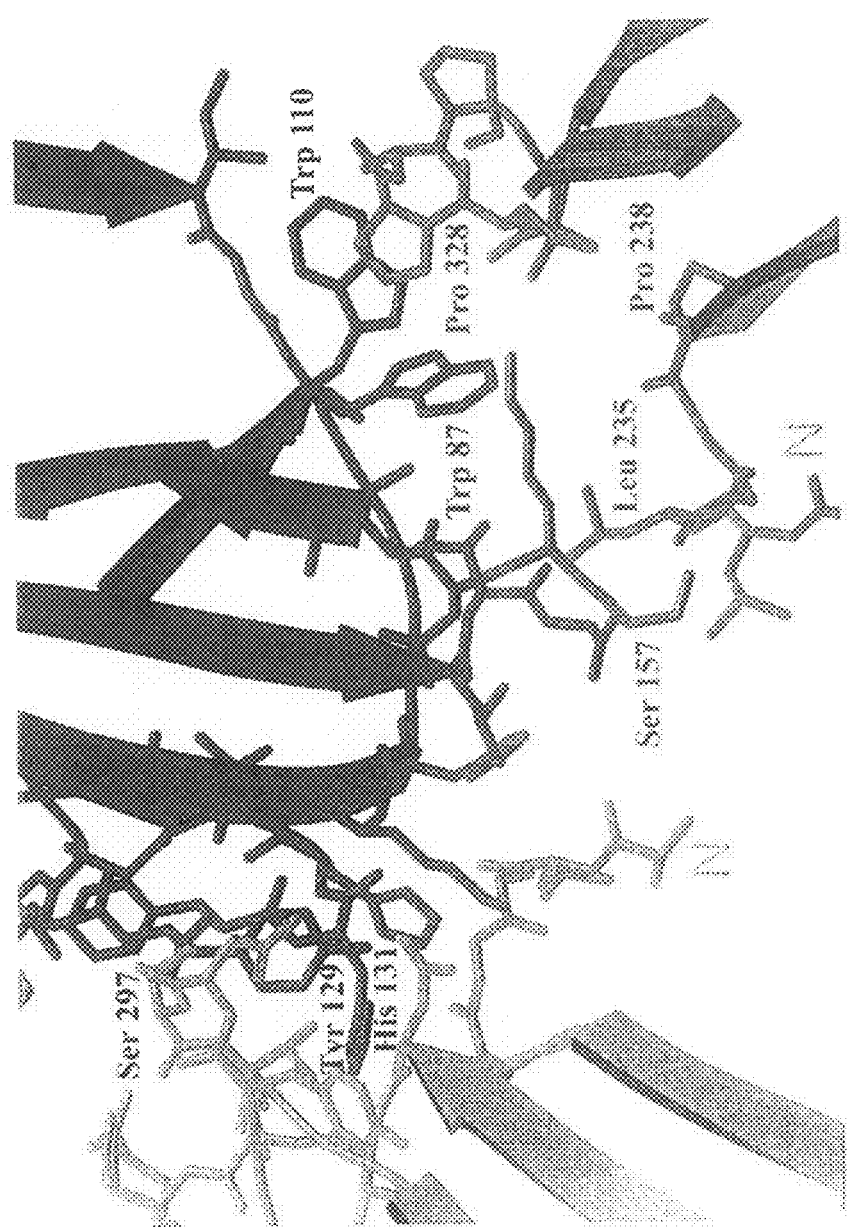

FIG. 9: Close-up on the binding region of the FcγRII and the Fc-fragment

The colour scheme is in agreement to FIG. 8 and residues important for complex formation are shown in ball-and-stick.

Figure 10A:
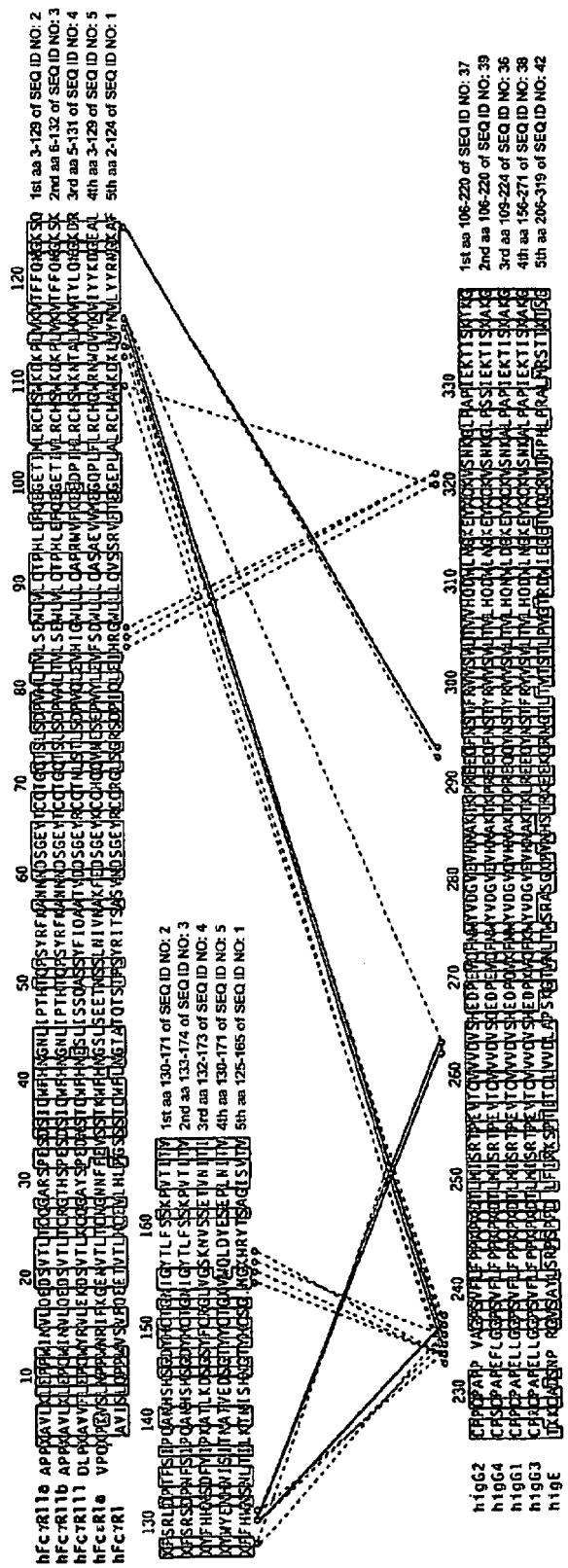

FIG. 10a:

In the upper part of FIG. 10a a structure based sequence alignment of the Fc-Receptor ecto-domains is shown. The sequences are FcγRIIa SEQ ID NO:2 (aa 3-129), FcγRIIb SEQ ID NO:3 (aa 6-132), FcγRIIIFcεRIa SEQ ID NO:4 (aa 5-131), FcεRIa SEQ ID NO:5 (aa 3-129), and SEQ ID NO:1 (aa 2-124), from top to bottom. Conserved residues are shaded yellow and identical residues orange. The sequences in the middle part of the figure are continued from their respective sequences in the top part of the figure. The lower part of the figure shows a part of the alignment of human antibody sequences. The sequences are hIgG2 SEQ ID NO:37 (aa 106-220), hIgG4 SEQ ID NO:39 (aa 106-220), hIgG1 SEQ ID NO:36 (aa 109-224), hIgG3 SEQ ID NO:38 (aa 156-271), and hIgE SEQ ID NO:42 (aa 206-319), from top to bottom. Residues of the human FcγRIII in contact with the Fc-fragment in the complex crystal structure are connected by lines (black for hydrophobic interaction, red for salt bridges and blue for hydrogenbridges). Residues from the Fc-receptor in contact with the A-chain of the Fc-fragment are connected with dashed lines and those in contact with the B-chain of the Fc-fragment with solid lines. Red, blue and black lines represent charged, polar and other contacts, respectively.

Figure 10B:
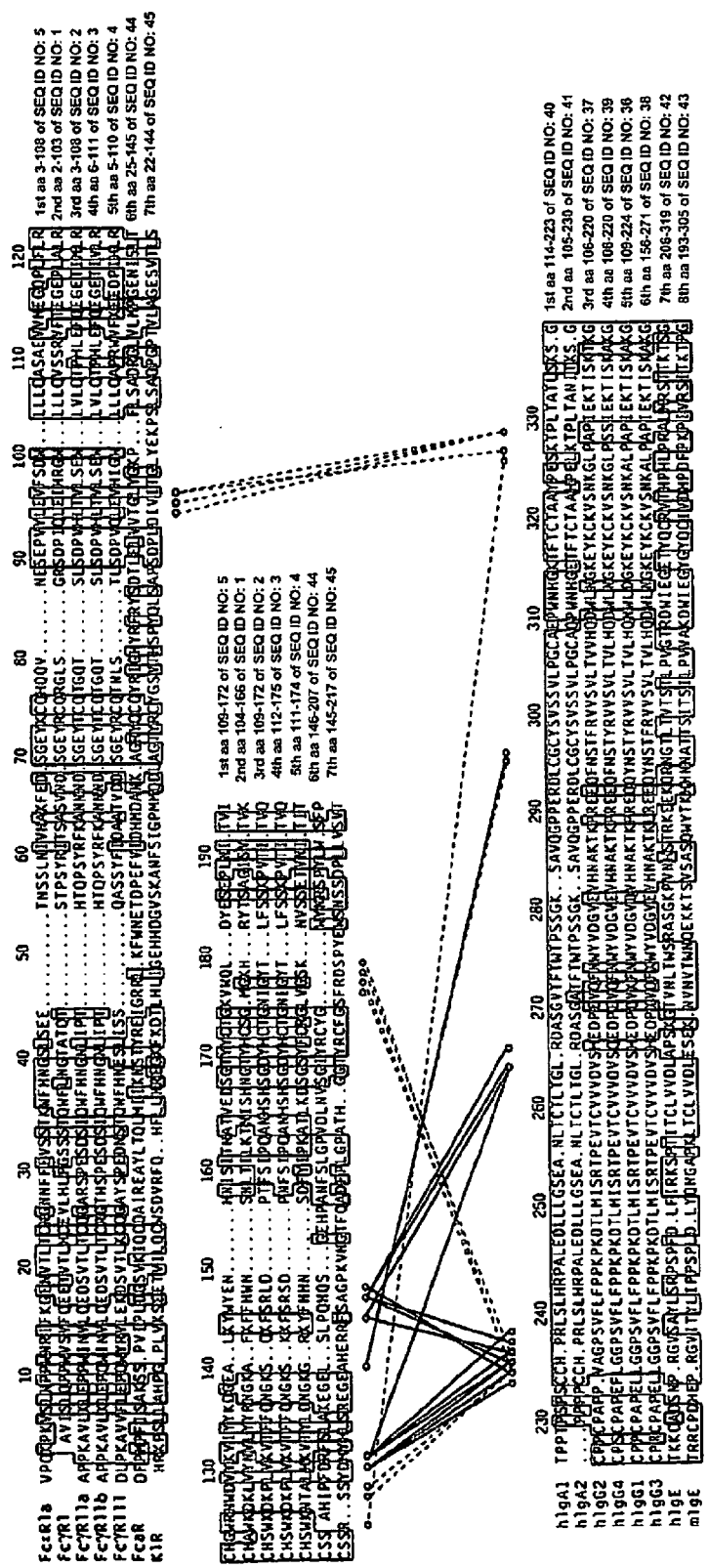

FIG. 10b:

In the upper part of FIG. 10b a structure based sequence alignment of the Fc-Receptor ecto-domains is shown. The sequences are FcεRIa SEQ ID NO:5 (aa 3-108), FcγRI SEQ ID NO:1 (aa 2-103), FcγRIIa SEQ ID NO:2 (aa 3-108), FcγRIIb SEQ ID NO:3 (aa 6-111), FcγRIII SEQ ID NO:4 (aa 5-110), FcA-receptor SEQ ID NO:44 (aa 22-145), Kir Receptor SEQ ID NO:45 (aa 22-144), from top to bottom. Conserved residues are shaded yellow and identical residues orange. The sequences in the middle part of the figure are continued from their respective sequences in the top part of the figure. Conserved residues within the less related Kir and FcA-Receptor sequences are shaded blue. The lower part of the figure shows a part of the alignment of human antibodies with the mouse IgE (migE) sequence. The sequences are hIgA1 SEQ ID NO:40 (aa 114-223), hIgA2 SEQ ID NO:41 (aa 105-230), hIgG2 SEQ ID NO:37 (aa 106-220), hIgG4 SEQ ID NO:39 (aa 106-220), hIgG1 SEQ ID NO:36 (aa 109-224), hIgG3 SEQ ID NO:38 (aa 156-271), hIgE SEQ ID NO:42 (aa 206-319), mIgE SEQ ID NO:43 (aa 193-305), from top to bottom. Residues of the human FcγRII in contact with the Fc-fragment in the complex crystal structure are connected by lines (black for hydrophobic interaction, red for salt bridges and blue for hydrogen bonds). Residues from the Fc-receptor in contact with the A-chain of the Fc-fragment are connected with dashed lines and those in contact with the B-chain of the Fc-fragment with solid lines. Red, blue and black lines represent charged, polar and other contacts, respectively.

FIG. 11 and FIG. 12:

FIG. 11 shows an alignment of the produced sFcγR, sFcεRIa and the short form of sFcεRII. FIG. 12 shows an alignment of the produced sFcεR and FcεRIa.

TABLE 1

Crystallographic results
The obtained preliminary crystallographic data are shown in this table.

|  | Orthorhombic | Tetragonal | Hexagonal |
|---|---|---|---|
| Space group | P2₁2₁2₁ [19] | P4₂2₁2 [94] | P3 [143] |
| Unit cell dimensions | a = 40.8 Å, b = 50.9 Å, c = 80.5 Å, α = 90°, β = 90°, γ = 90° | a = 85.7 Å, b = 85.7 Å, c = 63.4 Å, α = 90°, β = 90°, γ = 90° | a = 80.9 Å, b = 80.9 Å, c = 157.0 Å, α = 90°, β = 90°, γ = 90° |
| $R_{merge}$ | 5.8% | 9.8% | 13.6% |
| Resolution | 1.7 Å | 2.7 Å | 3.8 Å |
| Unique | 18,040 | 6,616 | 7,210 |
| Completeness | 89.1% | 97.1% | 63.0% |
| Multiplicity | 3.5 | 4.4 | 1.3 |
| $V_M$, molecules per asymmetric unit, solvent content | 2.09 Å³/Da, 1 mol., 41% solvent | 2.91 Å/Da, 1 mol, 58% solvent | 2.97 Å/Da, 5 mol, 59% solvent |

TABLE 2

Data collection statistics

| Derivative | Space Group | No. of unique reflections | Multiplicity | Resolution (Å) | Completeness (overall/last shell) (%/%) | $R_m$ (%) | No. of sites | Phasing power |
|---|---|---|---|---|---|---|---|---|
| NATI | P2₁2₁2₁ | 18009 | 3.6 | 1.74 | 92.9/86.4 | 5.5 | | |
| NATI | P4₂2₁2 | 6615 | 4.5 | 2.70 | 97.1/94.3 | 10.1 | | |
| NATI-Baculo | P3₁21 | 3545 | 2.5 | 3.0 | 93.0/98.9 | 14.4 | | |
| UOAc | P2₁2₁2₁ | 7722 | 4.2 | 2.1 | 96.8/95.7 | 7.3 | 1 | 1.79 |
| PtPy | P2₁2₁2₁ | 5520 | 3.9 | 2.3 | 89.7/49.6 | 10.5 | 1 | 1.39 |

$R_m = \Sigma I/_h \sim </_h > I/\Sigma </_h >$

Phasing power: $<F_H>/E$, where $<F_H> = \Sigma(F_H^2/n)^{1/2}$ is the r.m.s heavy atom structure amplitude.

$E = \Sigma[(F_{PHC} - F_{PH})^2/n]^{1/2}$ is the residual lack of closure error with $F_{PH}$ being the structure factor amplitude and $F_{PHC} = |F + F_H|$ the calculated structure factor amplitude of the derivative.

TABLE 3

Refinement statistics

| Resolution range (Å) | 8.0-1.74 Å |
|---|---|
| No. of unique reflections (F > 0σ (F)) | 16252 |
| R factor | 19.4 |
| $R_{free}$* | 27.9 |
| No. of atoms per asymmetric unit | |
| protein | 1371 |
| solvent | 150 |
| Rms deviation from ideal geometry | |
| bond length (Å) | 0.009 |
| bond angle (°) | 2.007 |
| Average B factors (Å²) | |
| protein main chain | 18.8 |
| protein side chain | 25.2 |
| solvent | 36.7 |
| Rms deviation of bonded B factors (Å²) | 4.1 |

*$R_{free}$: 5% of the reflections were used as a reference data set and were not included in the refinement.

TABLE 4

Residues that contribute to the interdomain contact via side chains

| FcγRIIb | FcγRIIa | FcγRIII | FcγRI | FceRIa |
|---|---|---|---|---|
| Asn15 | Asn | Ser | Ser | Arg |
| Asp20 | Asp | Asp | Glu | Glu |
| Gln91 | Gln | Gln | Gln | Gln |
| His108 | His | His | His | His |
| Trp110 | Trp | Trp | Trp | Trp |

TABLE 5

Primers used for the amplification of the FcRs

| Construct | 5'-Primer | 3'-Primer |
|---|---|---|
| sFcγRI | 5'-CACCCATATGGCAGTGATCTCTTT-3' (SEQ ID NO: 22) | 5'-AGGACTCGAGACTAGACAGGAGTTGGTAAC-3' (SEQ ID NO: 23) |
| sFcγRIIa | 5'-ACAGTCATATGGCAGCTCCCC-3' (SEQ ID NO: 24) | 5'-AAAAAAAGCTTCAGGGCACTTGGAC-3' (SEQ ID NO: 25) |
| sFcγRIIb | 5'-AATTCCATGGGGACACCTGCAGCTCCC-3' (SEQ ID NO: 26) | 5'-CCCAGTGTCGACAGCCTAAATGATCCCC-3' (SEQ ID NO: 27) |
| sFcγRIII | 5'-AAAAAAACATATGCGGACTGAAG-3' (SEQ ID NO: 28) | 5'-AAAAAAGCTTAACCTTGAGTGATG-3' (SEQ ID NO: 29) |
| sFceRIa | 5'-GATGGCCATATGGCAGTCCCTCAG-3' (SEQ ID NO: 30) | 5'-CAATGGATCCTAAAATTGTAGCCAG-3' (SEQ ID NO: 31) |

TABLE 5-continued

Primers used for the amplification of the FcRs

| Construct | 5'-Primer | 3'-Primer |
|---|---|---|
| sFcεRII | 5'-AAAAAAA<u>CATAT</u>GGA GTTGCAGG-3' (SEQ ID NO: 32) | 5'-TGGCT<u>GGATC</u>CATGCTCAA G-3' (SEQ ID NO: 33) |

Introduced restriction sites are underlined, start- and stop-codons are depicted as bold-italics

TABLE 6

Refolding Conditions for the FcRs

| Construct | Buffer |
|---|---|
| sFcγRI (SEQ ID NO: 1) | 0.1M TRIS/HCl, 1.2M arginine, 150 mM NaCl, 5 mM GSH, 0.5 mM GSSG, 0.02% sodium azide, pH 8.0 |
| sFcγRIIa (SEQ ID NO: 2) | 0.1M TRIS/HCl, 1.4M arginine, 150 mM NaCl, 2 mM GSH, 0.5 mM GSSG, 0.02% sodium azide, pH 8.0 |
| sFcγRIIb (SEQ ID NO: 3) | 0.1M TRIS/HCl, 1.4M arginine, 150 mM NaCl, 5 mM GSH, 0.5 mM GSSG, 0.02% sodium azide, pH 8.0 |
| sFcγRIII (SEQ ID NO: 4) | 0.1M TRIS/HCl, 1.0M arginine, 150 mM NaCl, 2 mM GSH, 0.5 mM GSSG, 0.02% sodium azide, pH 8.0 |
| sFcεRIIb (SEQ ID NO: 3) | 0.1M TRIS/HCl, 0.8M arginine, 150 mM NaCl, 5 mM GSH, 0.5 mM GSSG, 0.02% sodium azide, pH 8.3 |

TABLE 7

Crystallisation Conditions for the FcRs

| Construct | Condition | Space group, cell constants | Resolution |
|---|---|---|---|
| sFcγRIIa (SEQ ID NO: 2) | 26% PEG 8000, 0.2M sodium acetate/acetic acid pH 4.6, 0.02% sodium azide | C2, a = 80.4 Å, b = 49.7 Å, c = 54.6 Å, a = g = 90°, b = 128.1° | 3.0 Å |
| sFcγRIIb (SEQ ID NO: 3) | 33% PEG 2000, 0.2M sodium acetate, 0.02% sodium azide, pH5.4 | P212121, a = 40.8 Å, b = 50.9 Å, c = 80.5 Å, a = b = g = 90° | 1.7 Å |
| sFcγRIII (SEQ ID NO:4) | 22% PEG 8000, 0.1M MES/TRIS pH 7.8, 0.02% sodium azide | P22121, a = 36.7 Å, b = 60.3 Å, c = 85.6 Å, a = b = g = 90° | 2.5 Å |
| sFcγRIII: hFc1 | 6% PEG 8000, 0.1M MES/TRIS pH 5.6, 0.2M Na/K tartrate, 0.02% sodium azide | P6522, a = b = 115.0 Å, c = 303.3 Å, a = b = 90°, g = 120° | 3.3 Å |

REFERENCES

Ades, E. W., Phillips, D. J., Shore, S. L., Gordon, D. S., LaVia, M. F., Black, C. M., Reimer, C. B. (1976), Analysis of mononuclear cell surfaces with fluoresceinated Staphylococcal protein A complexed with IgG antibody or heat-aggregated γ-globulin, J. Immunol, 117, 2119.

Allen J. M., Seed B.; "Nucleotide sequence of three cDNAs for the human high affinity Fc receptor (FcRI)"; Nucleic Acids Res. 16:11824-11824 (1988).

Amigorena, S., Bonnerot, C., Drake, J. R., Choquet, D., Hunziker, W., Guillet, J. G., Webster, P., Sautes, C., Meilman, I., Fridman, W. H. (1992), Cytoplasmic domain heterogeneity and functions of IgG Fc receptors in B lymphocytes, Science 256, 1808-1812.

Barton, G. C. (1993), ALSCRIPT: tool to format multiple sequence alignments, Prot. Eng. 6, 37-40.

Bazil, V. and Strominger, J. L. (1994), Metalloprotease and serine protease are involved in cleavage of CD43, CD44, and CD16 from stimulated human granulocytes, J. Immunol. 152, 1314-1322.

Brünger, A. T., Kuriyan, J., Karplus, M. (1987), Crystallographic R factor refinement by molecular dynamics, Science 35, 458-460.

Burmeister, W. P., Huber, A. H., Bjorkman, P. J. (1994), Crystal structure of the complex of rat neonatal Fc receptor with Fc, Nature 372, 379-383.

Ceuppens, J. L., Baroja, M. L., van Vaeck, F., Anderson, C. L. (1988), Defect in the membrane expression of high affinity 72 kD Fcγ receptors on phagocytic cells in four healthy subjects, J. Clin. Invest. 82, 571-578. Collaborative computational project Number 4 (1994), The CCP4 suite: Programs for protein crystallography, Acta crystallogr. D50, 760-763.

Deisenhofer, J., Jones, T. A., Huber, R., Sjodahl, J., Sjoquist, J. (1978), Crystallization, crystal structure analysis and atomic model of the complex formed by a human Fc fragment and fragment B of protein A from *Staphylococcus aureus*, Z. Phys. Chem. 359, 975-985.

Deisenhofer, J. (1981), Crystallographic refinement and atomic models of a human Fc fragment and its complex with fragment B of protein A from *Staphylococcus aureus* at 2.9- and 2.8A resolution, Biochemistry 20, 2361-2370.

Deisenhofer J., Colman P M., Huber R., Haupt H., Schwick G.; "Crystallographic structural studies of a human Fc-fragment. I. An electron-density map at 4 Å resolution and a partial model"; Hoppe-Seyler's Z. Physiol. Chem. 357: 435-445 (1976).

Dulau, L., Cheyrou, A., Aigle, M. (1989), Directed mutagenesis using PCR, Nucleic Acids Res. 17, 2873.

Ellman (1959), Tissue sulfhydryl groups, Arch. Biochem. Biophys. 82, 79-77.

Engelhardt, W., Geerds, C., Frey, J. (1990), Distribution, inducibility and biological function of the cloned and expressed human βFc receptor II, Eur. J. Immunol. 20, 1367-1377.

Engh, R. A. and Huber, R. (1991), Accurate bond and angle parameters for X-ray protein structure refinement, Acta crystallogr. A47, 392-400.

Fleit, H. B., Kobasiuk, C. D., Daly, C., Furie, R., Levy, P. C., Webster, R. O. (1992), A soluble form of FcγRIII is present in human serum and other body fluids and is elevated at sites of inflammation, Blood 79, 2721-2728.

Fridman, W. H., Bonnerot, C., Daeron, M., Amigorena, S., Teillaud, J.~L., Sautes, C. (1992), Structural bases of Fcγ receptor functions, Immunol. Rev. 125, 49-76.

Fridman, W. H., Teillaud, J.-L., Bouchard, C., Teillaud, C., Astier, A., Tartour, E., Galon, J., Mathiot, C., Sautès, C. (1993), Soluble Fcγreceptors, J. Leukocyte Biol. 54, 504-512.

Gabb, H. A., Jackson, A. M., Sternberg, M. J. E. (1997), Modelling protein docking using shape complementarity, electrostatics and biochemical information, J. Mol. Biol. 272, 106-120.

Galon, J., Bouchard, C., Fridman, W. H., Sautès, C. (1995), Ligands and biological activities of soluble Fcγ receptors, Immunol. Lett. 44, 175-181.

Genetics Computer Group (1994), Program Manual for the Wisconsin Package Version 8, Madison, Wis.

Gordon, J. at al., (1980), The molecules controlling B lymphocytes. Immunol. Today, 8: 339-344.

Grodberg, J. and Dunn, J. J. (1988), OmpT encodes the *Escherichia coli* outer membrane protease that cleaves T7 RNA polymerase during purification, J. Bacteriol. 170, 1245-1253.

Hogarth, P. M., Hulett, M. D., Ierino, F. L., Tate, B., Powell, M. S., Brinkworth, R. I. (1992), Identification of the immunoglobulin binding regions (IBR) of FcγRII and FcεRI, Immunol. Rev. 125, 21-35.

Homsy, J., Meyer, M., Tateno, M., Clarkson, S., Levy, J. A. (1989), The Fc and not CD4 receptor mediates antibody enhancement of HIV infection in human cells, Science 244, 1357-1360.

Hoover, R. G., Lary, C., Page, R., Travis, P., Owens, R., Flick, J., Kornbluth, J., Barlogie, B. (1995), Autoregulatory circuits in myeloma: Tumor cell cytotoxity mediated by soluble CD16, J. Clin, Invest. 95, 241-247.

Huber, R., Deisenhofer, J., Colman, P. M., Matsushima, M. and Palm, W. (1976), Crystallographic structure studies of an IgG molecule and an Fc fragment, Nature 264, 415-420.

Hulett, M. D., Witort, E., Brinkworth, R. I., McKenzie, I. F. C., Hogarth, P. M. (1994), Identification of the IgG binding site of the human low affinity receptor for IgG FcγRII, J. Biol. Chem., 269, 15287-15293.

Hulett, M. D., Witort, E., Brinkworth, R. I., McKenzie, I. F. C., Hogarth, P. M. (1995), Multiple regions of human FcγRII (CD32) contribute to the binding of IgG, J. Biol. Chem. 270, 21188-21194.

Ierino, F. L., Powell, M. S., McKenzie, I. F. C., Hogarth, P. M. (1993), Recombinant soluble human FcγRII: Production, characterization, and inhibition of the arthus reaction, J. Exp. Med. 178, 1617-1628.

Jancarik, J. and Kim, S. H. (1991), Sparse matrix sampling: A screening method for crystallization of proteins, J. Appl. Crystallogr. 24, 409-411.

Jones, T. A., Zou, J.-Y., Cowan, S. W., Kjeldgaard, M. (1991), Improved methods for building protein models in electron density maps and the location of errors in these models, Acta crystallogr. A47, 110-119.

Kikutani H., Inui S., Sato R., Barsumian E. L., Owaki H., Yamasaki K., Kaisho T., Uchibayashi N., Hardy R. R., Hirano T., Tsunasawa S., Sakiyama F., Suemura M., Kishimoto T.; "Molecular structure of human lymphocyte receptor for immunoglobulin E"; Cell 47(5):657-665 (1986).

Khayat, D., Soubrane, C., Andriew, J. M., Visonneau, S., Eme, D., Tourani, J. M., Beldjord, K., Weil, M., Fernandez, E., Jaquillat, C. (1990), Changes of soluble CD16 levels in serum of HIV patients: Correlation with clinical and biological prognostic factors, J. Infect. Dis. 161, 430-435.

Kochan J., Pettine L. F., Hakimi J., Kishi K., Kinet J. P.; "Isolation of the gene coding for the alpha subunit of the human high affinity IgE receptor"; Nucleic Acids Res. 16:3584-3584 (1988).

Simmons D., Seed B.; "The Fc-gamma receptor of natural killer cells is a phospholipid-linked membrane protein"; Nature 333:568-570 (1988).

Kraulis, P. J. (1991), MOLSCRIPT: a program to produce both detailed and schematic plots of protein structures, J. Appl. Cryst. 24, 946-950.

Leslie, A. G. W. (1997), Mosflm user guide, mosflm version 5.50, MAC Laboratory of Molecular Biology, Cambridge, UK.

Lessel, U. and Schomburg, D. (1994), Similarities between protein 3-D structures, Protein Eng. 7, 1175-1187.

Littaua, A., Kurane, I. and Ennis, F. A. (1990), Human IgG Fc receptor II mediates antibody-dependent enhancement of dengue virus infection, J. Immunol. 144, 3183-3186.

Lynch, R. G., Hagen, M., Mueller, A., Sandor, M. (1995), Potential role of FcγR in early development of murine lymphoid cells: Evidence for functional interaction between FcγR on pre-thymocytes and an alternative, non-Ig ligand on thymic stromal cells, Immunol. Lett. 44, 105-109.

Mathiot, C., Teillaud, J. L., Elmalek, M., Mosseri, L., Euller-Ziegler, L., Daragon, A., Grosbois, B., Michaux, J. L., Facon, T., Bernard, J. F., Duclos, B., Monconduit, M., Fridman, W. H. (1993), Correlation between serum soluble CD16 (sCD16) levels and disease stage in patients with multiple myeloma, J. Clin. Immunol. 13, 41-48.

Merritt, E. A. and Murphy, M. E. P. (1994), Raster3D Version 2.0. A program for photorealistic molecular graphics, Acta Cryst. D50, 869-873.

Metzger, H. (1992A), Transmembrane signaling: The joy of aggregation, J. Immunol. 149, 1477-1487.

Metzger, H. (1992B), The receptor with high affinity for Ig E, Immunol. Rev. 125, 37-48.

Müller, S, and Hoover, R. G. (1985), T cells with Fc receptors in myeloma; suppression of growth and secretion of MOPC-315 by T alpha cells, J. Immunol. 134, 644-7.

Nicholls, A., Sharp, K. A., Honig, B. (1991), Protein folding and association: insights from the interfacial and thermodynamic properties of hydrocarbons, Proteins 11, 281-296.

Poo, H., Kraus, J. C., Mayo-Bond, L., Todd, R. F., Petty, H. R. (1995), Interaction of Fcγ receptor IIIB with complement receptor type 3 in fibroblast transfectants: evidence from lateral diffusion and resonance energy transfer studies, J. Mol. Biol. 247, 597-603.

Rappaport, E. F., Cassel, D. L., Walterhouse, D. O., McKenzie, S. E., Surrey, S., Keller, M. A., Schreiber, A. D., Schwartz, E. (1993), A soluble form of the human Fc receptor FcγRIIa: cloning, transcript analysis and detection. Exp. Hematol. 21, 689-696.

Ravanel, K., Castelle, C., Defrance, T., Wild, T. F., Charron, D., Lotteau, V., Rabourdincombe, C. (1997), Measles virus nucleocapsid protein binds to FcγRII and inhibits human B cell antibody production. J. Exp. Med. 186, 269-278.

Roman, S., Moore, J. S., Darby, C., Muller, S., Hoover, R. G. (1988), Modulation of Ig gene expression by Ig binding factors. Suppression of alpha-H chain and lambda-2-L chain mRNA accumulation in MOPC-315 by IgA-binding factor, J. Immunology 140, 3622-30.

Sarfat, D. et al., (1988), Elevation of IgE-binding factors of serum in patients with B-cell derived chronic lymphocytic leukemia. Blood, 71: 94-98.

Sauer-Eriksson, A. E., Kleywegt, G. J., Uhlen, M., Jones, T. A. (1995), Crystal structure of the C2 fragment of streptococcal protein G in complex with the Fc domain of human IgG, Structure 3, 265-78.

Small, T., at al., (1990), B-cell differentiation following autologous, conventional or T-cell depleted bone marrow transplantation: a recapitulation of normal B-cell ontogeny. Blood, 76: 1647-1656.

Sondermann, P., Huber, R., Jacob, U. (19988), Preparation and crystallization of active soluble human FcγRIIb derived from *E. coli*, Protein Structure, submitted.

Sondermann, P., Kutscher, C., Jacob, U., Frey, J. (1998A), Characterization and crystallization of soluble human Fcγ recap for 11 isoforms produced in insect cells, Biochemistry, submitted.

Sondermann, P., Kutscher, C., Jacob, U., Frey, J., Analysis of complexes of IgG and soluble human Fcγ-Receptor II produced in insect cells and its crystallization, submitted.

Stangelin S., Stamenkovic I., Seed B.; "Isolation of cDNAs for two distinct human Fc receptors by ligand affinity cloning"; EMBO J. 7:1053-1059 (1988).

Tax, W. J. M., Willems, H. W., Reekers, P. P. M., Capel, P. J. A., Koene, R. A. P. (1983), Polymorphism in mitogenic effect of IgG1 monoclonal antibodies against T3 antigen on human T cells, Nature 304, 445-447.

Teillaud, J. L., Brunati, S., Elmalek, M., Astier, A., Nicaise, P., Moncuit, J., Mathiot, C., Job-Deslandre, C., Fridman, W. H. (1990), Involvement of FcR+ T cells and of IgG-BF in the control of myeloma cells, Mol. Immunol. 27, 1209-17.

Turk, D. (1992), Ph.D. Thesis, T U München, Germany.

Ulvestad, E., Metre, R., Tonder, O. (1988), IgG Fc receptors in sera from patients with Rheumatoid Arthritis and Systemic Lupus Erythematosus, Scand. J. Rheumatol., Suppl. 75, 203-208.

van de Winkel, J. G. J. and Capel, P. J. A. (1993), Human IgG Fc receptor heterogeneity: Molecular aspects and clinical implications, Immunol. Today 14, 215-221.

Varin, N., Sautès, C., Galinha, A., Even, J., Hogarth, P. M., Fridman, W. H. (1989), Recombinant soluble reseptors for the Fcγ portion inhibit antibody production in vitro, Eur. J. Immunol. 19, 2263-2268.

Yang, 2., Delgado, R., Xu, L., Todd, R. F., Nabel, E. G., Sanchez, A., Nabel, G. J. (1998), Distinct cellular interactions of secreted and transmembrane Ebola virus glycoproteins, Science 279, 983-984.

Zhou, M.-J., Todd, R. F., van de Winkel, J. G. J., Petty, H. R. (1993), Cocapping of the leukoadhesin molecules complement receptor type 3 and lymphocyte function-associated antigen-1 with Fcγ receptor III on human neutrophils. Possible role of lectin-like interactions, J. Immunol. 150, 3030-3041.

---

The invention claimed is:

1. A method of identifying an inhibitor of an Fcγ receptor molecule which lacks any of (i) a transmembrane domain, (ii) signal peptide and (iii) glycosylation, comprising the steps of:
   (a) obtaining a hexagonal crystal of a complex of an FcγRIII receptor molecule and hFc1, wherein the FcγRIII receptor molecule consists of SEQ ID NO:4, the immunoglobulin is hFc1, and the complex is FcγRIII:hFc1, wherein the crystal is in space group $P6_522$, with unit cell dimensions of about a=b=115.0 Å, c=303.3 Å, a=b=90° and γ=120°;
   (b) determining the three-dimensional structure of said complex using the crystal of (a) by the X-ray diffraction method;
   (c) displaying the three dimensional structure of said complex on a performing computer by inputting said crystal structure data of said complex, wherein the performing computer comprises a computer program to generate said three dimensional structure and to identify an inhibitor; and
   (d) selecting an inhibitor complementary to FcγRIII receptor binding site of an immunoglobulin molecule.

2. A method for identifying an inhibitor of an Fcγ receptor molecule which lacks any of (i) a transmembrane domain, (ii) signal peptide and (iii) glycosylation, comprising the steps of:
   (a) obtaining a hexagonal crystal of a complex of an FcγRIII receptor molecule and hFc1, wherein the FcγRIII receptor molecule consists of SEQ ID NO:4, the immunoglobulin is hFc1, and the complex is FcγRIII:hFc1, wherein the crystal is in space group $P6_522$, with unit cell dimensions of about a=b=115.0 Å, c=303.3 Å, a=b=90° and γ=120°;
   (b) determining the three-dimensional structure of said complex using the crystal of (a) by the X-ray diffraction method;
   (c) displaying the three dimensional structure of said complex on a performing computer by inputting said crystal structure data from said complex, wherein the performing computer comprises a computer program to generate said three dimensional structure and to identify an inhibitor; and
   (d) selecting an inhibitor complementary to immunoglobulin binding site of said receptor molecule.

* * * * *

SEQUENCE LISTING

```
<160> NUMBER OF SEQ ID NOS: 45

<210> SEQ ID NO 1
<211> LENGTH: 269
<212> TYPE: PRT
<213> ORGANISM: Homo sapiens

<400> SEQUENCE: 1

Met Ala Val Ile Ser Leu Gln Pro Pro Trp Val Ser Val Phe Gln Glu
1               5                   10                  15

Glu Thr Val Thr Leu His Cys Glu Val Leu His Leu Pro Gly Ser Ser
                20                  25                  30

Ser Thr Gln Trp Phe Leu Asn Gly Thr Ala Thr Gln Thr Ser Thr Pro
            35                  40                  45

Ser Tyr Arg Ile Thr Ser Ala Ser Val Asn Asp Ser Gly Glu Tyr Arg
        50                  55                  60

Cys Gln Arg Gly Leu Ser Gly Arg Ser Asp Pro Ile Gln Leu Glu Ile
65                  70                  75                  80

His Arg Gly Trp Leu Leu Leu Gln Val Ser Ser Arg Val Phe Thr Glu
                85                  90                  95

Gly Glu Pro Leu Ala Leu Arg Cys His Ala Trp Lys Asp Lys Leu Val
                100                 105                 110

Tyr Asn Val Leu Tyr Tyr Arg Asn Gly Lys Ala Phe Lys Phe His
            115                 120                 125

Trp Asn Ser Asn Leu Thr Ile Leu Lys Thr Asn Ile Ser His Asn Gly
        130                 135                 140

Thr Tyr His Cys Ser Gly Met Gly Lys His Arg Tyr Thr Ser Ala Gly
145                 150                 155                 160

Ile Ser Val Thr Val Lys Glu Leu Phe Pro Ala Pro Val Leu Asn Ala
                165                 170                 175

Ser Val Thr Ser Pro Leu Leu Glu Gly Asn Leu Val Thr Leu Ser Cys
            180                 185                 190

Glu Thr Lys Leu Leu Leu Gln Arg Pro Gly Leu Gln Leu Tyr Phe Ser
        195                 200                 205

Phe Tyr Met Gly Ser Lys Thr Leu Arg Gly Arg Asn Thr Ser Ser Glu
    210                 215                 220

Tyr Gln Ile Leu Thr Ala Arg Arg Glu Asp Ser Gly Leu Tyr Trp Cys
225                 230                 235                 240
```

Glu Ala Ala Thr Glu Asp Gly Asn Val Leu Lys Arg Ser Pro Glu Leu
            245                 250                 255

Glu Leu Gln Val Leu Gly Leu Gln Leu Pro Thr Pro Val
        260                 265

<210> SEQ ID NO 2
<211> LENGTH: 174
<212> TYPE: PRT
<213> ORGANISM: Homo sapiens

<400> SEQUENCE: 2

Met Ala Ala Pro Pro Lys Ala Val Leu Lys Leu Glu Pro Pro Trp Ile
1               5                   10                  15

Asn Val Leu Gln Glu Asp Ser Val Thr Leu Thr Cys Gln Gly Ala Arg
            20                  25                  30

Ser Pro Glu Ser Asp Ser Ile Gln Trp Phe His Asn Gly Asn Leu Ile
        35                  40                  45

Pro Thr His Thr Gln Pro Ser Tyr Arg Phe Lys Ala Asn Asn Asn Asp
    50                  55                  60

Ser Gly Glu Tyr Thr Cys Gln Thr Gly Gln Thr Ser Leu Ser Asp Pro
65                  70                  75                  80

Val His Leu Thr Val Leu Ser Glu Trp Leu Val Leu Gln Thr Pro His
                85                  90                  95

Leu Glu Phe Gln Glu Gly Glu Thr Ile Met Leu Arg Cys His Ser Trp
            100                 105                 110

Lys Asp Lys Pro Leu Val Lys Val Thr Phe Phe Gln Asn Gly Lys Ser
        115                 120                 125

Gln Lys Phe Ser Arg Leu Asp Pro Thr Phe Ser Ile Pro Gln Ala Asn
    130                 135                 140

His Ser His Ser Gly Asp Tyr His Cys Thr Gly Asn Ile Gly Tyr Thr
145                 150                 155                 160

Leu Phe Ser Ser Lys Pro Val Thr Ile Thr Val Gln Val Pro
                165                 170

<210> SEQ ID NO 3
<211> LENGTH: 185
<212> TYPE: PRT
<213> ORGANISM: Homo sapiens

<400> SEQUENCE: 3

Met Gly Thr Pro Ala Ala Pro Pro Lys Ala Val Leu Lys Leu Glu Pro
1               5                   10                  15

Gln Trp Ile Asn Val Leu Gln Glu Asp Ser Val Thr Leu Thr Cys Arg
            20                  25                  30

Gly Thr His Ser Pro Glu Ser Asp Ser Ile Gln Trp Phe His Asn Gly
        35                  40                  45

Asn Leu Ile Pro Thr His Thr Gln Pro Ser Tyr Arg Phe Lys Ala Asn
    50                  55                  60

Asn Asn Asp Ser Gly Glu Tyr Thr Cys Gln Thr Gly Gln Thr Ser Leu
65                  70                  75                  80

Ser Asp Pro Val His Leu Thr Val Leu Ser Glu Trp Leu Val Leu Gln
                85                  90                  95

Thr Pro His Leu Glu Phe Gln Glu Gly Glu Thr Ile Val Leu Arg Cys
            100                 105                 110

His Ser Trp Lys Asp Lys Pro Leu Val Lys Val Thr Phe Phe Gln Asn
        115                 120                 125

```
Gly Lys Ser Lys Lys Phe Ser Arg Ser Asp Pro Asn Phe Ser Ile Pro
            130                 135                 140
Gln Ala Asn His Ser His Ser Gly Asp Tyr His Cys Thr Gly Asn Ile
145                 150                 155                 160
Gly Tyr Thr Leu Tyr Ser Ser Lys Pro Val Thr Ile Thr Val Gln Ala
                165                 170                 175
Pro Ser Ser Ser Pro Met Gly Ile Ile
                180                 185

<210> SEQ ID NO 4
<211> LENGTH: 176
<212> TYPE: PRT
<213> ORGANISM: Homo sapiens

<400> SEQUENCE: 4

Met Arg Thr Glu Asp Leu Pro Lys Ala Val Val Phe Leu Glu Pro Gln
1               5                   10                  15
Trp Tyr Ser Val Leu Glu Lys Asp Ser Val Thr Leu Lys Cys Gln Gly
                20                  25                  30
Ala Tyr Ser Pro Glu Asp Asn Ser Thr Gln Trp Phe His Asn Glu Ser
            35                  40                  45
Leu Ile Ser Ser Gln Ala Ser Ser Tyr Phe Ile Asp Ala Ala Thr Val
50                  55                  60
Asn Asp Ser Gly Glu Tyr Arg Cys Gln Thr Asn Leu Ser Thr Leu Ser
65                  70                  75                  80
Asp Pro Val Gln Leu Glu Val His Ile Gly Trp Leu Leu Leu Gln Ala
                85                  90                  95
Pro Arg Trp Val Phe Lys Glu Glu Asp Pro Ile His Leu Arg Cys His
            100                 105                 110
Ser Trp Lys Asn Thr Ala Leu His Lys Val Thr Tyr Leu Gln Asn Gly
        115                 120                 125
Lys Asp Arg Lys Tyr Phe His His Asn Ser Asp Phe His Ile Pro Lys
    130                 135                 140
Ala Thr Leu Lys Asp Ser Gly Ser Tyr Phe Cys Arg Gly Leu Val Gly
145                 150                 155                 160
Ser Lys Asn Val Ser Ser Glu Thr Val Asn Ile Thr Ile Thr Gln Gly
                165                 170                 175

<210> SEQ ID NO 5
<211> LENGTH: 183
<212> TYPE: PRT
<213> ORGANISM: Homo sapiens

<400> SEQUENCE: 5

Met Ala Val Pro Gln Lys Pro Lys Val Ser Leu Asn Pro Pro Trp Asn
1               5                   10                  15
Arg Ile Phe Lys Gly Glu Asn Val Thr Leu Thr Cys Asn Gly Asn Asn
                20                  25                  30
Phe Phe Glu Val Ser Ser Thr Lys Trp Phe His Asn Gly Ser Leu Ser
            35                  40                  45
Glu Glu Thr Asn Ser Ser Leu Asn Ile Val Asn Ala Lys Phe Glu Asp
        50                  55                  60
Ser Gly Glu Tyr Lys Cys Gln His Gln Gln Val Asn Glu Ser Glu Pro
65                  70                  75                  80
Val Tyr Leu Glu Val Phe Ser Asp Trp Leu Leu Leu Gln Ala Ser Ala
                85                  90                  95
```

```
Glu Val Val Met Glu Gly Gln Pro Leu Phe Leu Arg Cys His Gly Trp
            100                 105                 110

Arg Asn Trp Asp Val Tyr Lys Val Ile Tyr Tyr Lys Asp Gly Glu Ala
        115                 120                 125

Leu Lys Tyr Trp Tyr Glu Asn His Asn Ile Ser Ile Thr Asn Ala Thr
    130                 135                 140

Val Glu Asp Ser Gly Thr Tyr Tyr Cys Thr Gly Lys Val Trp Gln Leu
145                 150                 155                 160

Asp Tyr Glu Ser Glu Pro Leu Asn Ile Thr Val Ile Lys Ala Pro Arg
                165                 170                 175

Glu Lys Tyr Trp Leu Gln Phe
            180

<210> SEQ ID NO 6
<211> LENGTH: 275
<212> TYPE: PRT
<213> ORGANISM: Homo sapiens

<400> SEQUENCE: 6

Met Asp Thr Thr Gln Ser Leu Lys Gln Leu Glu Glu Arg Ala Ala Arg
1               5                   10                  15

Asn Val Ser Gln Val Ser Lys Asn Leu Glu Ser His His Gly Asp Gln
            20                  25                  30

Met Thr Gln Lys Ser Gln Ser Thr Gln Ile Ser Gln Glu Leu Glu Glu
        35                  40                  45

Leu Arg Ala Glu Gln Gln Arg Leu Lys Ser Gln Asp Leu Glu Leu Ser
    50                  55                  60

Trp Asn Leu Asn Gly Leu Gln Ala Asp Leu Ser Ser Phe Lys Ser Gln
65                  70                  75                  80

Glu Leu Asn Glu Arg Asn Glu Ala Ser Asp Leu Leu Glu Arg Leu Arg
                85                  90                  95

Glu Glu Val Thr Lys Leu Arg Met Glu Leu Gln Val Ser Ser Gly Phe
            100                 105                 110

Val Cys Asn Thr Cys Pro Glu Lys Trp Ile Asn Phe Gln Arg Lys Cys
        115                 120                 125

Tyr Tyr Phe Gly Lys Gly Thr Lys Gln Trp Val His Ala Arg Tyr Ala
    130                 135                 140

Cys Asp Asp Met Glu Gly Gln Leu Val Ser Ile His Ser Pro Glu Glu
145                 150                 155                 160

Gln Asp Phe Leu Thr Lys His Ala Ser His Thr Gly Ser Trp Ile Gly
                165                 170                 175

Leu Arg Asn Leu Asp Leu Lys Gly Glu Phe Ile Trp Val Asp Gly Ser
            180                 185                 190

His Val Asp Tyr Ser Asn Trp Ala Pro Gly Glu Pro Thr Ser Arg Ser
        195                 200                 205

Gln Gly Glu Asp Cys Val Met Met Arg Gly Ser Gly Arg Trp Asn Asp
    210                 215                 220

Ala Phe Cys Asp Arg Lys Leu Gly Ala Trp Val Cys Asp Arg Leu Ala
225                 230                 235                 240

Thr Cys Thr Pro Pro Ala Ser Glu Gly Ser Ala Glu Ser Met Gly Pro
                245                 250                 255

Asp Ser Arg Pro Asp Pro Asp Gly Arg Leu Pro Thr Pro Ser Ala Pro
            260                 265                 270

Leu His Ser
275
```

```
<210> SEQ ID NO 7
<211> LENGTH: 820
<212> TYPE: DNA
<213> ORGANISM: Homo sapiens

<400> SEQUENCE: 7
catatggcag tgatctcttt gcagcctcca tgggtcagcg tgttccaaga ggaaaccgta        60
accttgcact gtgaggtgct ccatctgcct gggagcagct ctacacagtg gtttctcaat       120
ggcacagcca ctcagacctc gaccccagc tacagaatca cctctgccag tgtcaatgac       180
agtggtgaat acaggtgcca gagaggtctc tcagggcgaa gtgacccat acagctggaa       240 atccacagag gctggctact actgcaggtc tccagcagag tcttcacgga aggagaacct       300
ctggccttga ggtgtcatgc gtggaaggat aagctggtgt acaatgtgct ttactatcga       360
aatggcaaag cctttaagtt tttccactgg aattctaacc tcaccattct gaaaaccaac       420
ataagtcaca atggcaccta ccattgctca ggcatgggaa agcatcgcta cacatcagca       480
ggaatatctg tcactgtgaa agagctattt ccagctccag tgctgaatgc atctgtgaca       540
tccccactcc tggaggggaa tctggtcacc ctgagctgtg aaacaaagtt gctcttgcag       600
aggcctggtt tgcagcttta cttctccttc tacatgggca gcaagaccct gcgaggcagg       660
aacacatcct ctgaatacca aatactaact gctagaagag aagactctgg gttatactgg       720
tgcgaggctg ccacagagga tgaaaatgtc cttaagcgca gccctgagtt ggagcttcaa       780
gtgcttggcc tccagttacc aactcctgtc tagtctcgag                             820

<210> SEQ ID NO 8
<211> LENGTH: 533
<212> TYPE: DNA
<213> ORGANISM: Homo sapiens

<400> SEQUENCE: 8
catatggcag ctcccccaaa ggctgtgctg aaacttgagc cccgtggat caacgtgctc         60 caggaggact ctgtgactct gacatgccag ggggctcgca gccctgagag cgactccatt       120
cagtggttcc acaatgggaa tctcattccc acccacacgc agcccagcta caggttcaag       180
gccaacaaca atgacagcgg ggagtacacg tgccagactg gccagaccag cctcagcgac       240
cctgtgcatc tgactgtgct ttccgaatgg ctggtgctcc agaccctca cctggagttc       300 caggagggag aaaccatcat gctgaggtgc acagctgga aggacaagcc tctggtcaag       360
gtcacattct tccagaatgg aaatccag aaattctccc gtttggatcc caccttctcc       420
atcccacaag caaaccacag tcacagtggt gattaccact gcacaggaaa cataggctac       480
acgctgttct catccaagcc tgtgaccatc actgtccaag tgccctgaag ctt             533

<210> SEQ ID NO 9
<211> LENGTH: 569
<212> TYPE: DNA
<213> ORGANISM: Homo sapiens

<400> SEQUENCE: 9
ccatggggac acctgcagct cccccaaagg ctgtgctgaa actcgagccc agtggatca         60 acgtgctcca ggaggactct gtgactctga catgccgggg gactcacagc cctgagagcg       120
actccattca gtggttccac aatgggaatc tcattcccac ccacgcag cccagctaca       180 ggttcaaggc caacaacaat gacagcgggg agtacacgtg ccagactggc agaccagcc       240 tcagcgaccc tgtgcatctg actgtgcttt ctgagtggct ggtgctccag accctcacc       300 tggagttcca ggagggagaa accatcgtgc tgaggtgcca cagctggaag acaagcctc       360
```

```
tggtcaaggt cacattcttc cagaatggaa atccaagaa attttcccgt tcggatccca    420
acttctccat cccacaagca aaccacagtc acagtggtga ttaccactgc acaggaaaca    480
taggctacac gctgtactca tccaagcctg tgaccatcac tgtccaagct cccagctctt    540
caccgatggg gatcatttag gctgtcgac                                      569

<210> SEQ ID NO 10
<211> LENGTH: 538
<212> TYPE: DNA
<213> ORGANISM: Homo sapiens

<400> SEQUENCE: 10
catatgcgga ctgaagatct cccaaaggct gtggtgttcc tggagcctca atggtacagc    60
gtgcttgaga aggacagtgt gactctgaag tgccagggag cctactcccc tgaggacaat    120
tccacacagt ggtttcacaa tgagagcctc atctcaagcc aggcctcgag ctacttcatt    180
gacgctgcca cagtcaacga cagtggagag tacaggtgcc agacaaacct ctccaccctc    240
agtgacccgg tgcagctaga agtccatatc ggctggctgt tgctccaggc ccctcggtgg    300
gtgttcaagg aggaagaccc tattcacctg aggtgtcaca gctggaagaa cactgctctg    360
cataaggtca catatttaca gaatggcaaa gacaggaagt attttcatca taattctgac    420
ttccacattc caaaagccac actcaaagat agcggctcct acttctgcag ggggcttgtt    480
gggagtaaaa atgtgtcttc agagactgtg aacatcacca tcactcaagg ttaagctt     538

<210> SEQ ID NO 11
<211> LENGTH: 560
<212> TYPE: DNA
<213> ORGANISM: Homo sapiens

<400> SEQUENCE: 11
catatggcag tccctcagaa acctaaggtc tccttgaacc ctccatggaa tagaatattt    60
aaaggagaga atgtgactct tacatgtaat gggaacaatt tctttgaagt cagttccacc    120
aaatggttcc acaatggcag cctttcagaa gagacaaatt caagtttgaa tattgtgaat    180
gccaaatttg aagacagtgg agaatacaaa tgtcagcacc aacaagttaa tgagagtgaa    240
cctgtgtacc tggaagtctt cagtgactgg ctgctccttc aggcctctgc tgaggtggtg    300
atggagggcc agcccctctt cctcaggtgc catggttgga ggaactggga tgtgtacaag    360
gtgatctatt ataaggatgg tgaagctctc aagtactggt atgagaacca caacatctcc    420
attacaaatg ccacagttga agacagtgga acctactact gtacgggcaa agtgtggcag    480
ctggactatg agtctgagcc cctcaacatt actgtaataa aagctccgcg tgagaagtac    540
tggctacaat tttaggatcc                                               560

<210> SEQ ID NO 12
<211> LENGTH: 532
<212> TYPE: DNA
<213> ORGANISM: Homo sapiens

<400> SEQUENCE: 12
catatggagt tgcaggtgtc cagcggcttt gtgtgcaaca cgtgccctga aaagtggatc    60
aatttccaac ggaagtgcta ctacttcggc aagggcacca agcagtgggt ccacgcccgg    120
tatgcctgtg acgacatgga agggcagctg tcagcatcca cagcccggag ggagcaggac    180
ttcctgacca gcatgccagc ccacaccggc tcctggattg ccttcggaaa cttgacctga    240 aaggggggagt ttatctgggt ggatgggagc cacgtggact acagcaactg ggctccaggg    300
```

| | |
|---|---|
| gagcccacca gccggagcca gggcgaggac tgcgtgatga tgcggggctc cggtcgctgg | 360 |
| aacgacgcct tctgcgaccg taagctgggc gcctgggtgt gcgaccggct ggccacatgc | 420 |
| acgccgccag ccagcgaagg ttccgcggag tccatgggac ctgattcaag accagaccct | 480 |
| gacggccgcc tgcccacccc ctctgcccct ctccactctt gagcatggat cc | 532 |

<210> SEQ ID NO 13
<211> LENGTH: 1419
<212> TYPE: DNA
<213> ORGANISM: Homo sapiens

<400> SEQUENCE: 13

| | |
|---|---|
| ggctgtgact gctgtgctct gggcgccact cgctccaggg agtgatggga atcctgtcat | 60 |
| ttttacctgt ccttgccact gagagtgact gggctgactg caagtccccc cagccttggg | 120 |
| gtcatatgct tctgtggaca gctgtgctat tcctggctcc tgttgctggg acacctgcag | 180 |
| ctcccccaaa ggctgtgctg aaactcgagc cccagtggat caacgtgctc caggaggact | 240 |
| ctgtgactct gacatgccgg gggactcaca gccctgagag cgactccatt cagtggttcc | 300 |
| acaatgggaa tctcattccc acccacacgc agcccagcta caggttcaag gccaacaaca | 360 |
| atgacagcgg ggagtacacg tgccagactg gccagaccag cctcagcgac cctgtgcatc | 420 |
| tgacagtgct ttctgagtgg ctggtgctcc agacccctca cctggagttc caggagggag | 480 |
| aaaccatcgt gctgaggtgc acagctgga aggacaagcc tctggtcaag gtcacattct | 540 |
| tccagaatgg aaaatccaag aaatttttcc cgttcggatc caacttctcc atcccacaag | 600 |
| caaaccacag tcacagtggt gattaccatt gcacaggaaa cataggctac acgctgtact | 660 |
| catccaagcc tgtgaccatc actgtccaag ctcccagctc ttcaccgatg gggatcattg | 720 |
| tggctgtggt cactgggatt gctgtagctg ccattgttgc tgctgtagtg gccttgatct | 780 |
| actgcaggaa aaagcggatt tcagccaatc ccactaatcc tgatgaggct gacaaagttg | 840 |
| gggctgagaa cacaatcacc tattcacttc tcatgcaccc ggatgctctg gaagagcctg | 900 |
| atgaccagaa ccgtatttag tctccattgt cttgcattgg gatttgagaa gaaatcagag | 960 |
| agggaagatc tggtatttcc tggcctaaat tccccttggg gaggacaggg agatgctgca | 1020 |
| gttccaaaag agaaggtttc ttccagagtc atctacctga gtcctgaagc tccctgtcct | 1080 |
| gaaagccaca gacaatatgg tcccaaatgc ccgactgcac cttctgtgct tcagctcttc | 1140 |
| ttgacatcaa ggctcttccg ttccacatcc acacagccaa tccaattaat caaaccactg | 1200 |
| ttattaacag ataatagcaa cttgggaaat gcttatgtta caggttacgt gagaacaatc | 1260 |
| atgtaaatct atatgatttc agaaatgtta aaatagacta acctctacca gcacattaaa | 1320 |
| agtgattgtt tctgggtgat aaaattattg atgattttta ttttctttat ttttctataa | 1380 |
| agatcatata ttacttttat aataaaacat tataaaaac | 1419 |

<210> SEQ ID NO 14
<211> LENGTH: 1068
<212> TYPE: DNA
<213> ORGANISM: Homo sapiens

<400> SEQUENCE: 14

| | |
|---|---|
| agatctcagc acagtaagca ccaggagtcc atgaagaaga tggctcctgc catggaatcc | 60 |
| cctactctac tgtgtgtagc cttactgttc ttcgctccag atggcgtgtt agcagtccct | 120 |
| cagaaaccta aggtctcctt gaaccctcca tggaatagaa tatttaaagg agagaatgtg | 180 |
| actcttacat gtaatgggaa caatttcttt gaagtcagtt ccaccaaatg gttccacaat | 240 |

-continued

```
ggcagcctttt cagaagagac aaattcaagt ttgaatattg tgaatgccaa atttgaagac    300
agtggagaat acaaatgtca gcaccaacaa gttaatgaga gtgaacctgt gtacctggaa    360
gtcttcagtg actggctgct ccttcaggcc tctgctgagg tggtgatgga gggccagccc    420
ctcttcctca ggtgccatgg ttggaggaac tgggatgtgt acaaggtgat ctattataag    480
gatggtgaag ctctcaagta ctggtatgag aaccacaaca tctccattac aaatgccaca    540
gttgaagaca gtggaaccta ctactgtacg ggcaaagtgt ggcagctgga ctatgagtct    600
gagcccctca acattactgt aataaaagct ccgcgtgaga agtactggct acaattttt     660 atcccattgt tggtggtgat tctgtttgct gtggacacag gattatttat ctcaactcag    720
cagcaggtca catttctctt gaagattaag agaaccagga aaggcttcag acttctgaac    780
ccacatccta agccaaaccc caaaaacaac tgatataatt aactcaagaa atatttgcaa    840 cattagttttt tttccagcat cagcaattgc tactcaattg tcaaacacag cttgcaatat    900
acatagaaac gtctgtgctc aaggatttat agaaatgctt cattaaactg agtgaaactg    960
attaagtggc atgtaatagt aagtgctcaa ttaacattgg ttgaataaat gagagaatga   1020
atagattcat ttattagcat ttgtaaaaga gatgttcaat ttagatct                1068

<210> SEQ ID NO 15
<211> LENGTH: 1321
<212> TYPE: DNA
<213> ORGANISM: Homo sapiens

<400> SEQUENCE: 15
gacagatttc actgctccca ccagcttgga gacaacatgt ggttcttgac aactctgctc     60
ctttgggttc cagttgatgg gcaagtggac accacaaagg cagtgatctc tttgcagcct    120
ccatgggtca gcgtgttcca agaggaaacc gtaaccttgc actgtgaggt gctccatctg    180
cctgggagca gctctacaca gtggtttctc aatggcacag ccactcagac ctcgaccccc    240
agctacagaa tcacctctgc cagtgtcaat gacagtggtg aatacaggtg ccagagaggt    300
ctctcagggc gaagtgaccc catacagctg gaaatccaca gaggctggct actactgcag    360
gtctccagca gagtcttcac ggaaggagaa ccctctggcct tgaggtgtca tgcgtggaag    420
gataagctgg tgtacaatgt gcttttactat cgaaatggca aagcctttaa gttttttccac    480 tggaattcta acctcaccat tctgaaaacc aacataagtc acaatggcac ctaccattgc    540
tcaggcatgg gaaagcatcg ctacacatca gcaggaatat ctgtcactgt gaaagagcta    600
tttccagctc cagtgctgaa tgcatctgtg acatccccac tcctggaggg gaatctggtc    660
accctgagct gtgaaacaaa gttgctcttg cagaggcctg gtttgcagct ttacttctcc    720
ttctacatgg gcagcaagac cctgcgaggc aggaacacat cctctgaata ccaaatacta    780
actgctagaa gagaagactc tgggttatac tggtgcgagg ctgccacaga ggatggaaat    840
gtccttaagc gcagccctga gttggagctt caagtgcttg gcctccagtt accaactcct    900 gtctggttc atgtcctttt ctatctggca gtgggaataa tgttttttagt gaacactgtt    960 ctctgggtga caatacgtaa agaactgaaa gaaagaaaa agtgggattt agaaatctct   1020
ttggattctg gtcatgagaa gaaggtaact tccagccttc aagaagacag acatttagaa   1080
gaagagctga aatgtcagga acaaaaagaa gaacagctgc aggaaggggt gcaccggaag   1140 gagcccagg ggccacgta gcagcggctc agtgggtggc catcgatctg gaccgtcccc    1200
tgcccacttg ctccccgtga gcactgcgta caaacatcca aaagttcaac aacaccagaa   1260
```

-continued

```
ctgtgtgtct catggtatgt aactcttaaa gcaaataaat gaactgactt caaaaaaaaa      1320
a                                                                       1321
```

<210> SEQ ID NO 16
<211> LENGTH: 2359
<212> TYPE: DNA
<213> ORGANISM: Homo sapiens

<400> SEQUENCE: 16

```
cccaaatgtc tcagaatgta tgtcccagaa acctgtggct gcttcaacca ttgacagttt       60
tgctgctgct ggcttctgca gacagtcaag ctgcagctcc cccaaaggct gtgctgaaac      120
ttgagccccc gtggatcaac gtgctccagg aggactctgt gactctgaca tgccagggg      180
ctcgcagccc tgagagcgac tccattcagt ggttccacaa tgggaatctc attcccaccc      240
acacgcagcc cagctacagg ttcaaggcca caacaatga cagcggggag tacacgtgcc      300
agactggcca gaccagcctc agcgaccctg tgcatctgac tgtgctttcc gaatggctgg      360
tgctccagac ccctcacctg gagttccagg agggagaaac catcatgctg aggtgccaca      420
gctggaagga caagcctctg tcaaggtca cattcttcca gaatgaaaaa tcccagaat       480
tctcccgttt ggatcccacc ttctccatcc acaagcaaa ccacagtcac agtggtgatt       540
accactgcac aggaaacata ggctacacgc tgttctcatc caagcctgtg accatcactg      600
tccaagtgcc cagcatgggc agctcttcac caatggggat cattgtggct gtggtcattg      660
cgactgctgt agcagccatt gttgctgctg tagtggcctt gatctactgc aggaaaaagc      720
ggatttcagc caattccact gatcctgtga aggctgccca atttgagcca cctggacgtc      780
aaatgattgc catcagaaag agacaacttg aagaaaccaa caatgactat gaaacagctg      840
acggcggcta catgactctg aaccccaggg cacctactga cgatgataaa aacatctacc      900
tgactcttcc tcccaacgac catgtcaaca gtaataacta agagtaacg ttatgccatg       960
tggtcatact ctcagcttgc tgatggatga caaaagagg ggaattgtta aaggaaaatt      1020
taaatggaga ctggaaaaat cctgagcaaa caaaccacc tggcccttag aaatagcttt      1080
aactttgctt aaactacaaa cacaagcaaa acttcacggg gtcatactac atacaagcat      1140
aagcaaaact taacttggat catttctggt aaatgcttat gttagaaata agacaacccc      1200
agccaatcac aagcagccta ctaacatata attaggtgac tagggacttt ctaagaagat      1260
acctaccccc aaaaaacaat tatgtaattg aaaaccaacc gattgccttt attttgcttc      1320
cacattttcc caataaatac ttgcctgtga cattttgcca ctggaacact aaacttcatg      1380
aattgcgcct cagatttttc ctttaacatc tttttttttt ttgacagagt ctcaatctgt      1440
tacccaggct ggagtgcagt ggtgctatct tggctcactg caaacccgcc tcccaggttt      1500
aagcgattct tatgcctcag cctcccagta gctgggatta gaggcatgtg ccatcatacc      1560
cagctaattt ttgtattttt tattttttat tttagtaga cagggtttt cgcaatgttg       1620
gccaggccga tctcgaactt ctggcctcta gcgatctgcc cgcctcggcc tcccaaagtg      1680
ctgggatgac cgcatcagcc ccaatgtcca gcctctttaa catcttcttt cctatgccct      1740
ctctgtggat ccctactgct ggtttctgcc ttctccatgc tgagaacaaa atcacctatt      1800
cactgcttat gcagtcggaa gctccagaag aacaaagagc ccaattacca gaaccacatt      1860
aagtctccat tgttttgcct tgggatttga gaagagaatt agagaggtga ggatctggta      1920
tttcctggac taaattccct tggggaagac gaagggatgc tgcagttcca aaagagaagg      1980
actcttccag agtcatctac ctgagtccca aagctccctg tcctgaaagc cacagacaat      2040
```

-continued

| | |
|---|---|
| atggtcccaa atgactgact gcaccttctg tgcctcagcc gttcttgaca tcaagaatct | 2100 |
| tctgttccac atccacacag ccaatacaat tagtcaaacc actgttatta acagatgtag | 2160 |
| caacatgaga aacgcttatg ttacaggtta catgagagca atcatgtaag tctatatgac | 2220 |
| ttcagaaatg ttaaaataga ctaacctcta acaacaaatt aaaagtgatt gtttcaaggt | 2280 |
| gatgcaatta ttgatgacct attttatttt tctataatga tcatatatta cctttgtaat | 2340 |
| aaaacattat aaccaaaac | 2359 |

<210> SEQ ID NO 17
<211> LENGTH: 887
<212> TYPE: DNA
<213> ORGANISM: Homo sapiens

<400> SEQUENCE: 17

| | |
|---|---|
| tctttggtga cttgtccact ccagtgtggc atcatgtggc agctgctcct cccaactgct | 60 |
| ctgctacttc tagtttcagc tggcatgcgg actgaagatc tcccaaaggc tgtggtgttc | 120 |
| ctggagcctc aatggtacag cgtgcttgag aaggacagtg tgactctgaa gtgccaggga | 180 |
| gcctactccc ctgaggacaa ttccacacag tggtttcaca atgagagcct catctcaagc | 240 |
| caggcctcga gctacttcat tgacgctgcc acagtcaacg acagtggaga gtacaggtgc | 300 |
| cagacaaacc tctccaccct cagtgacccg gtgcagctag aagtccatat cggctggctg | 360 |
| ttgctccagg cccctcggtg ggtgttcaag gaggaagacc ctattcacct gaggtgtcac | 420 |
| agctggaaga acactgctct gcataaggtc acatatttac agaatggcaa agacaggaag | 480 |
| tattttcatc ataattctga cttccacatt ccaaaagcca cactcaaaga tagcggctcc | 540 |
| tacttctgca gggggcttgt tgggagtaaa aatgtgtctt cagagactgt gaacatcacc | 600 |
| atcactcaag gtttggcagt gtcaaccatc tcatcattct ctccacctgg gtaccaagtc | 660 |
| tctttctgct tggtgatggt actccttttt gcagtggaca caggactata tttctctgtg | 720 |
| aagacaaaca tttgaagctc aacaagagac tggaaggacc ataaacttaa atggagaaag | 780 |
| gaccctcaag acaaatgacc cccatcccat gggagtaata agagcagtgg cagcagcatc | 840 |
| tctgaacatt tctctggatt tgcaacccca tcatcctcag gcctctc | 887 |

<210> SEQ ID NO 18
<211> LENGTH: 1503
<212> TYPE: DNA
<213> ORGANISM: Homo sapiens

<400> SEQUENCE: 18

| | |
|---|---|
| ctcctgctta aacctctgtc tctgacggtc cctgccaatc gctctggtcg accccaacac | 60 |
| actaggagga cagacacagg ctccaaactc cactaagtga ccagagctgt gattgtgccc | 120 |
| gctgagtgga ctgcgttgtc agggagtgag tgctccatca tcgggagaat ccaagcagga | 180 |
| ccgccatggg ggaaggtcaa tattcagaga tcgaggagct tcccaggagg cggtgttgca | 240 |
| ggcgtgggac tcagatcgtg ctgctgggc tggtgaccgc cgctctgtgg gctgggctgc | 300 |
| tgactctgct tctcctgtgg cactgggaca ccacacagag tctaaaacag ctggaagaga | 360 |
| gggctgcccg gaacgtctct caagtttcca agaacttgga aagccaccac ggtgaccaga | 420 |
| tggcgcagaa atcccagtcc acgcagattt cacaggaact ggaggaactt cgagctgaac | 480 |
| agcagagatt gaaatctcag gacttggagc tgtcctggaa cctgaacggg cttcaagcag | 540 |
| atctgagcag cttcaagtcc caggaattga acgagaggaa cgaagcttca gatttgctgg | 600 |
| aaagactccg ggaggaggtg acaaagctaa ggatggagtt gcaggtgtcc agcggctttg | 660 |

-continued

```
tgtgcaacac gtgccctgaa aagtggatca atttccaacg gaagtgctac tacttcggca    720
agggcaccaa gcagtgggtc cacgcccggt atgcctgtga cgacatggaa gggcagctgg    780
tcagcatcca cagcccggag gagcaggact cctgaccaa gcatgccagc cacaccggct     840
cctggattgg ccttcggaac ttggacctga agggagagtt tatctgggtg atgggagcc    900 atgtggacta cagcaactgg gctccagggg agcccaccag ccggagccag gcgaggact    960 gcgtgatgat gcggggctcc ggtcgctgga cgacgccctt ctgcgaccgt aagctgggcg   1020
cctgggtgtg cgaccggctg ccacatgca cgccgccagc cagcgaaggt tccgcggagt    1080
ccatgggacc tgattcaaga ccagaccctg acggccgcct gcccaccccc tctgcccctc   1140
tccactcttg agcatggata cagccaggcc cagagcaaga ccctgaagac ccccaaccac   1200
ggcctaaaag cctctttgtg gctgaaaggt ccctgtgaca ttttctgcca cccaaacgga   1260
ggcagctgac acatctcccg ctcctctatg gcccctgcct tcccaggagt acacccccaac  1320 agcaccctct ccagatggga gtgccccccaa cagcaccctc tccagatgag agtacacccc   1380
aacagcaccc tctccagatg cagccccatc tcctcagcac cccaggacct gagtatcccc   1440
agctcaggtg gtgagtcctc ctgtccagcc tgcatcaata aaatggggca gtgatggcct   1500
ccc                                                                 1503

<210> SEQ ID NO 19
<211> LENGTH: 32
<212> TYPE: DNA
<213> ORGANISM: Artificial sequence
<220> FEATURE:
<223> OTHER INFORMATION: Primer for Fc(gamma)RIIb2

<400> SEQUENCE: 19
aatagaattc catggggaca cctgcagctc cc                                  32

<210> SEQ ID NO 20
<211> LENGTH: 28
<212> TYPE: DNA
<213> ORGANISM: Artificial sequence
<220> FEATURE:
<223> OTHER INFORMATION: Primer for Fc(gamma)RIIb2

<400> SEQUENCE: 20
cccagtgtcg acagcctaaa tgatcccc                                       28

<210> SEQ ID NO 21
<211> LENGTH: 6
<212> TYPE: PRT
<213> ORGANISM: Artificial sequence
<220> FEATURE:
<223> OTHER INFORMATION: N terminal sequence of shFc?RIIb

<400> SEQUENCE: 21

Gly Thr Pro Ala Ala Pro
              5

<210> SEQ ID NO 22
<211> LENGTH: 24
<212> TYPE: DNA
<213> ORGANISM: Artificial sequence
<220> FEATURE:
<223> OTHER INFORMATION: 5' primer for sFc?RI

<400> SEQUENCE: 22
cacccatatg gcagtgatct cttt                                           24
```

-continued

```
<210> SEQ ID NO 23
<211> LENGTH: 30
<212> TYPE: DNA
<213> ORGANISM: Artificial sequence
<220> FEATURE:
<223> OTHER INFORMATION: 3' primer for sFc?RI

<400> SEQUENCE: 23
aggactcgag actagacagg agttggtaac                                         30

<210> SEQ ID NO 24
<211> LENGTH: 21
<212> TYPE: DNA
<213> ORGANISM: Artificial sequence
<220> FEATURE:
<223> OTHER INFORMATION: 5' primer for sFc?RIIb

<400> SEQUENCE: 24
acagtcatat ggcagctccc c                                                  21

<210> SEQ ID NO 25
<211> LENGTH: 25
<212> TYPE: DNA
<213> ORGANISM: Artificial sequence
<220> FEATURE:
<223> OTHER INFORMATION: 3' primer for sFc?RII6

<400> SEQUENCE: 25
aaaaaaagct tcagggcact tggac                                              25

<210> SEQ ID NO 26
<211> LENGTH: 27
<212> TYPE: DNA
<213> ORGANISM: Artificial sequence
<220> FEATURE:
<223> OTHER INFORMATION: 5' primer for sFc?RIIb

<400> SEQUENCE: 26
aattcaatgg ggacacctgc agctccc                                            27

<210> SEQ ID NO 27
<211> LENGTH: 28
<212> TYPE: DNA
<213> ORGANISM: Artificial sequence
<220> FEATURE:
<223> OTHER INFORMATION: 5' primer for sFc?RIIb

<400> SEQUENCE: 27
cccagtgtcg acagcctaaa tgatcccc                                           28

<210> SEQ ID NO 28
<211> LENGTH: 23
<212> TYPE: DNA
<213> ORGANISM: Artificial sequence
<220> FEATURE:
<223> OTHER INFORMATION: 5' primer for sFc?RIIb

<400> SEQUENCE: 28
aaaaaaacat atgcggactg aag                                                23

<210> SEQ ID NO 29
<211> LENGTH: 24
<212> TYPE: DNA
<213> ORGANISM: Artificial sequence
<220> FEATURE:
<223> OTHER INFORMATION: 3' primer for sFc?RIIb
```

-continued

```
<400> SEQUENCE: 29
aaaaaagctt aaccttgagt gatg                                              24

<210> SEQ ID NO 30
<211> LENGTH: 23
<212> TYPE: DNA
<213> ORGANISM: Artificial sequence
<220> FEATURE:
<223> OTHER INFORMATION: 5' primer for sFceRIa

<400> SEQUENCE: 30
gatggccata ggcagtccct cag                                               23

<210> SEQ ID NO 31
<211> LENGTH: 25
<212> TYPE: DNA
<213> ORGANISM: Artificial sequence
<220> FEATURE:
<223> OTHER INFORMATION: 3' primer for sFceRIa

<400> SEQUENCE: 31
caatggatcc taaaattgta gccag                                             25

<210> SEQ ID NO 32
<211> LENGTH: 23
<212> TYPE: DNA
<213> ORGANISM: Artificial sequence
<220> FEATURE:
<223> OTHER INFORMATION: 5' primer for FceRII

<400> SEQUENCE: 32
aaaaaaacat atggagttgc agg                                               23

<210> SEQ ID NO 33
<211> LENGTH: 20
<212> TYPE: DNA
<213> ORGANISM: Artificial sequence
<220> FEATURE:
<223> OTHER INFORMATION: 3' primer for sFceRII

<400> SEQUENCE: 33
tggctggatc catgctcaag                                                   20

<210> SEQ ID NO 34
<211> LENGTH: 221
<212> TYPE: PRT
<213> ORGANISM: Homo sapiens

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

-continued

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys
    210                 215                 220

<210> SEQ ID NO 35
<211> LENGTH: 109
<212> TYPE: PRT
<213> ORGANISM: Homo sapiens

<400> SEQUENCE: 35

Ala Lys Gly Gln Pro Arg Glu Pro Gln Val Tyr Thr Leu Pro Pro Ser
1               5                   10                  15

Arg Asp Glu Leu Thr Lys Asn Gln Val Ser Leu Thr Cys Leu Val Lys
            20                  25                  30

Gly Phe Tyr Pro Ser Asp Ile Ala Val Glu Trp Glu Ser Asn Gly Gln
        35                  40                  45

Pro Glu Asn Asn Tyr Lys Thr Thr Pro Pro Val Leu Asp Ser Asp Gly
    50                  55                  60

Ser Phe Phe Leu Tyr Ser Lys Leu Thr Val Asp Lys Ser Arg Trp Gln
65                  70                  75                  80

Gln Gly Asn Val Phe Ser Cys Ser Val Met His Glu Ala Leu His Asn
                85                  90                  95

His Tyr Thr Gln Lys Ser Leu Ser Leu Ser Pro Gly Lys
            100                 105

<210> SEQ ID NO 36
<211> LENGTH: 330
<212> TYPE: PRT
<213> ORGANISM: Homo sapiens

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 37
<211> LENGTH: 300
<212> TYPE: PRT
<213> ORGANISM: Homo sapiens

<400> SEQUENCE: 37

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160
```

```
Val Glu Val His Asn Ala Lys Thr Lys Pro Arg Glu Gln Phe Asn
            165                 170                 175

Ser Thr Phe Arg Val Val Ser Val Leu Thr Val Val His Gln Asp Trp
        180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ser Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
    275                 280                 285

Leu Thr Val Asp Lys Ser Arg Trp Gln Gln Gly Asn
            290                 295                 300

<210> SEQ ID NO 38
<211> LENGTH: 377
<212> TYPE: PRT
<213> ORGANISM: Homo sapiens

<400> SEQUENCE: 38

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240
```

```
Gln Asp Trp Leu Asn Gly Lys Glu Tyr Lys Cys Lys Val Ser Asn Lys
                245                 250                 255
Ala Leu Pro Ala Pro Ile Glu Lys Thr Ile Ser Lys Ala Lys Gly Gln
                260                 265                 270
Pro Arg Glu Pro Gln Val Tyr Thr Leu Pro Pro Ser Arg Glu Glu Met
            275                 280                 285
Thr Lys Asn Gln Val Ser Leu Thr Cys Leu Val Lys Gly Phe Tyr Pro
        290                 295                 300
Ser Asp Ile Ala Val Glu Trp Glu Ser Ser Gly Gln Pro Glu Asn Asn
305                 310                 315                 320
Tyr Asn Thr Thr Pro Pro Met Leu Asp Ser Asp Gly Ser Phe Phe Leu
                325                 330                 335
Tyr Ser Lys Leu Thr Val Asp Lys Ser Arg Trp Gln Gln Gly Asn Ile
            340                 345                 350
Phe Ser Cys Ser Val Met His Glu Ala Leu His Asn Arg Phe Thr Gln
        355                 360                 365
Lys Ser Leu Ser Leu Ser Pro Gly Lys
    370                 375

<210> SEQ ID NO 39
<211> LENGTH: 327
<212> TYPE: PRT
<213> ORGANISM: Homo sapiens

<400> SEQUENCE: 39

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Glu Met Thr Lys
225                 230                 235                 240
```

```
Asn Gln Val Ser Leu Thr Cys Leu Val Lys Gly Phe Tyr Pro Ser Asp
                    245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 40
<211> LENGTH: 353
<212> TYPE: PRT
<213> ORGANISM: Homo sapiens

<400> SEQUENCE: 40

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285
```

-continued

```
Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
                340                 345                 350

Tyr

<210> SEQ ID NO 41
<211> LENGTH: 340
<212> TYPE: PRT
<213> ORGANISM: Homo sapiens

<400> SEQUENCE: 41

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
                20                  25                  30

Pro Gln Glu Pro Leu Ser Val Thr Trp Ser Glu Ser Gly Gln Asn Val
            35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Cys Cys His Pro
                100                 105                 110

Arg Leu Ser Leu His Arg Pro Ala Leu Glu Asp Leu Leu Leu Gly Ser
            115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
    195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
    275                 280                 285

Ala Glu Asp Trp Lys Lys Gly Asp Thr Phe Ser Cys Met Val Gly His
    290                 295                 300
```

```
Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 42
<211> LENGTH: 428
<212> TYPE: PRT
<213> ORGANISM: Homo sapiens

<400> SEQUENCE: 42

Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Trp Asp Thr Gly Ser Leu
        35                  40                  45

Asn Gly Thr Thr Met Thr Leu Pro Ala Thr Thr Leu Thr Leu Ser Gly
50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
                85                  90                  95

Val Asp Asn Lys Thr Phe Ser Val Cys Ser Arg Asp Phe Thr Pro Pro
            100                 105                 110

Thr Val Lys Ile Leu Gln Ser Ser Cys Asp Gly Gly Gly His Phe Pro
        115                 120                 125

Pro Thr Ile Gln Leu Leu Cys Leu Val Ser Gly Tyr Thr Pro Gly Thr
130                 135                 140

Ile Asn Ile Thr Trp Leu Glu Asp Gly Gln Val Met Asp Val Asp Leu
145                 150                 155                 160

Ser Thr Ala Ser Thr Thr Gln Glu Gly Glu Leu Ala Ser Thr Gln Ser
                165                 170                 175

Glu Leu Thr Leu Ser Gln Lys His Trp Leu Ser Asp Arg Thr Tyr Thr
            180                 185                 190

Cys Gln Val Thr Tyr Gln Gly His Thr Phe Glu Asp Ser Thr Lys Lys
        195                 200                 205

Cys Ala Asp Ser Asn Pro Arg Gly Val Ser Ala Tyr Leu Ser Arg Pro
210                 215                 220

Ser Pro Phe Asp Leu Phe Ile Arg Lys Ser Pro Thr Ile Thr Cys Leu
225                 230                 235                 240

Val Val Asp Leu Ala Pro Ser Lys Gly Thr Val Asn Leu Thr Trp Ser
                245                 250                 255

Arg Ala Ser Gly Lys Pro Val Asn His Ser Thr Arg Lys Glu Glu Lys
            260                 265                 270

Gln Arg Asn Gly Thr Leu Thr Val Thr Ser Thr Leu Pro Val Gly Thr
        275                 280                 285

Arg Asp Trp Ile Glu Gly Glu Thr Tyr Gln Cys Arg Val Thr His Pro
290                 295                 300

His Leu Pro Arg Ala Leu Met Arg Ser Thr Thr Lys Thr Ser Gly Pro
305                 310                 315                 320

Arg Ala Ala Pro Glu Val Tyr Ala Phe Ala Thr Pro Glu Trp Pro Gly
                325                 330                 335
```

```
Ser Arg Asp Lys Arg Thr Leu Ala Cys Leu Ile Gln Asn Phe Met Pro
            340                 345                 350

Glu Asp Ile Ser Val Gln Trp Leu His Asn Glu Val Gln Leu Pro Asp
            355                 360                 365

Ala Arg His Ser Thr Thr Gln Pro Arg Lys Thr Lys Gly Ser Gly Phe
370                 375                 380

Phe Val Phe Ser Arg Leu Glu Val Thr Arg Ala Glu Trp Glu Gln Lys
385                 390                 395                 400

Asp Glu Phe Ile Cys Arg Ala Val His Glu Ala Ala Ser Pro Ser Gln
            405                 410                 415

Thr Val Gln Arg Ala Val Ser Val Asn Pro Gly Lys
            420                 425

<210> SEQ ID NO 43
<211> LENGTH: 421
<212> TYPE: PRT
<213> ORGANISM: Homo sapiens

<400> SEQUENCE: 43

Ser Ile Arg Asn Pro Gln Leu Tyr Pro Leu Lys Pro Cys Lys Gly Thr
1               5                   10                  15

Ala Ser Met Thr Leu Gly Cys Leu Val Lys Asp Tyr Phe Pro Asn Pro
            20                  25                  30

Val Thr Val Thr Trp Tyr Ser Asp Ser Leu Asn Met Ser Thr Val Asn
        35                  40                  45

Phe Pro Ala Leu Gly Ser Glu Leu Lys Val Thr Thr Ser Gln Val Thr
    50                  55                  60

Ser Trp Gly Lys Ser Ala Lys Asn Phe Thr Cys His Val Thr His Pro
65                  70                  75                  80

Pro Ser Phe Asn Glu Ser Arg Thr Ile Leu Val Arg Pro Val Asn Ile
                85                  90                  95

Thr Glu Pro Thr Leu Glu Leu Leu His Ser Ser Cys Asp Pro Asn Ala
            100                 105                 110

Phe His Ser Thr Ile Gln Leu Tyr Cys Phe Ile Tyr Gly His Ile Leu
        115                 120                 125

Asn Asp Val Ser Val Ser Trp Leu Met Asp Asp Arg Glu Ile Thr Asp
    130                 135                 140

Thr Leu Ala Gln Thr Val Leu Ile Lys Glu Glu Gly Lys Leu Ala Ser
145                 150                 155                 160

Thr Cys Ser Lys Leu Asn Ile Thr Glu Gln Gln Trp Met Ser Glu Ser
                165                 170                 175

Thr Phe Thr Cys Lys Val Thr Ser Gln Gly Val Asp Tyr Leu Ala His
            180                 185                 190

Thr Arg Arg Cys Pro Asp His Glu Pro Arg Gly Val Ile Thr Tyr Leu
        195                 200                 205

Ile Pro Pro Ser Pro Leu Asp Leu Tyr Gln Asn Gly Ala Pro Lys Leu
    210                 215                 220

Thr Cys Leu Val Val Asp Leu Glu Ser Glu Lys Asn Val Asn Val Thr
225                 230                 235                 240

Trp Asn Gln Glu Lys Lys Thr Ser Val Ser Ala Ser Gln Trp Tyr Thr
                245                 250                 255

Lys His His Asn Asn Ala Thr Thr Ser Ile Thr Ser Ile Leu Pro Val
            260                 265                 270

Val Ala Lys Asp Trp Ile Glu Gly Tyr Gly Tyr Gln Cys Ile Val Asp
        275                 280                 285
```

```
His Pro Asp Phe Pro Lys Pro Ile Val Arg Ser Ile Thr Lys Thr Pro
        290                 295                 300
Gly Gln Arg Ser Ala Pro Glu Val Tyr Val Phe Pro Pro Glu Glu
305                 310                 315                 320
Glu Ser Glu Asp Lys Arg Thr Leu Thr Cys Leu Ile Gln Asn Phe Phe
                    325                 330                 335
Pro Glu Asp Ile Ser Val Gln Trp Leu Gly Asp Gly Lys Leu Ile Ser
                340                 345                 350
Asn Ser Gln His Ser Thr Thr Pro Leu Lys Ser Asn Gly Ser Asn
            355                 360                 365
Gln Gly Phe Phe Ile Phe Ser Arg Leu Glu Val Ala Lys Thr Leu Trp
370                 375                 380
Thr Gln Arg Lys Gln Phe Thr Cys Gln Val Ile His Glu Ala Leu Gln
385                 390                 395                 400
Lys Pro Arg Lys Leu Glu Lys Thr Ile Ser Thr Ser Leu Gly Asn Thr
                405                 410                 415
Ser Leu Arg Pro Ser
            420

<210> SEQ ID NO 44
<211> LENGTH: 287
<212> TYPE: PRT
<213> ORGANISM: Homo sapiens

<400> SEQUENCE: 44

Met Asp Pro Lys Gln Thr Thr Leu Leu Cys Leu Val Leu Cys Leu Gly
1               5                   10                  15
Gln Arg Ile Gln Ala Gln Glu Gly Asp Phe Pro Met Pro Phe Ile Ser
                20                  25                  30
Ala Lys Ser Ser Pro Val Ile Pro Leu Asp Gly Ser Val Lys Ile Gln
                35                  40                  45
Cys Gln Ala Ile Arg Glu Ala Tyr Leu Thr Gln Leu Met Ile Ile Lys
        50                  55                  60
Asn Ser Thr Tyr Arg Glu Ile Gly Arg Arg Leu Lys Phe Trp Asn Glu
65                  70                  75                  80
Thr Asp Pro Glu Phe Val Ile Asp His Met Asp Ala Asn Lys Ala Gly
                85                  90                  95
Arg Tyr Gln Cys Gln Tyr Arg Ile Gly His Tyr Arg Phe Arg Tyr Ser
                100                 105                 110
Asp Thr Leu Glu Leu Val Val Thr Gly Leu Tyr Gly Lys Pro Phe Leu
            115                 120                 125
Ser Ala Asp Arg Gly Leu Val Leu Met Pro Gly Glu Asn Ile Ser Leu
130                 135                 140
Thr Cys Ser Ser Ala His Ile Pro Phe Asp Arg Phe Ser Leu Ala Lys
145                 150                 155                 160
Glu Gly Glu Leu Ser Leu Pro Gln His Gln Ser Gly Glu His Pro Ala
                165                 170                 175
Asn Phe Ser Leu Gly Pro Val Asp Leu Asn Val Ser Gly Ile Tyr Arg
            180                 185                 190
Cys Tyr Gly Trp Tyr Asn Arg Ser Pro Tyr Leu Trp Ser Phe Pro Ser
            195                 200                 205
Asn Ala Leu Glu Leu Val Val Thr Asp Ser Ile His Gln Asp Tyr Thr
        210                 215                 220
Thr Gln Asn Leu Ile Arg Met Ala Val Ala Gly Leu Val Leu Val Ala
225                 230                 235                 240
```

```
Leu Leu Ala Ile Leu Val Glu Asn Trp His Ser His Thr Ala Leu Asn
                245                 250                 255

Lys Glu Ala Ser Ala Asp Val Ala Glu Pro Ser Trp Ser Gln Gln Met
            260                 265                 270

Cys Gln Pro Gly Leu Thr Phe Ala Arg Thr Pro Ser Val Cys Lys
        275                 280                 285

<210> SEQ ID NO 45
<211> LENGTH: 337
<212> TYPE: PRT
<213> ORGANISM: Homo sapiens

<400> SEQUENCE: 45

Val Val Ser Met Val Cys Val Gly Phe Phe Leu Leu Gln Gly Ala Trp
1               5                   10                  15

Pro His Glu Gly Val His Arg Lys Pro Ser Leu Leu Ala His Pro Gly
            20                  25                  30

Pro Leu Val Lys Ser Glu Glu Thr Val Ile Leu Gln Cys Trp Ser Asp
        35                  40                  45

Val Arg Phe Gln His Phe Leu Leu His Arg Glu Gly Lys Phe Lys Asp
    50                  55                  60

Thr Leu His Leu Ile Gly Glu His His Asp Gly Val Ser Lys Ala Asn
65                  70                  75                  80

Phe Ser Ile Gly Pro Met Met Gln Asp Leu Ala Gly Thr Tyr Arg Cys
                85                  90                  95

Tyr Gly Ser Val Thr His Ser Pro Tyr Gln Leu Ser Ala Pro Ser Asp
            100                 105                 110

Pro Leu Asp Ile Val Ile Thr Gly Leu Tyr Glu Lys Pro Ser Leu Ser
        115                 120                 125

Ala Gln Pro Gly Pro Thr Val Leu Ala Gly Glu Ser Val Thr Leu Ser
    130                 135                 140

Cys Ser Ser Arg Ser Ser Tyr Asp Met Tyr His Leu Ser Arg Glu Gly
145                 150                 155                 160

Glu Ala His Glu Arg Arg Phe Ser Ala Gly Pro Lys Val Asn Gly Thr
                165                 170                 175

Phe Gln Ala Asp Phe Pro Leu Gly Pro Ala Thr His Gly Gly Thr Tyr
            180                 185                 190

Arg Cys Phe Gly Ser Phe Arg Asp Ser Pro Tyr Glu Trp Ser Asn Ser
        195                 200                 205

Ser Asp Pro Leu Leu Val Ser Val Thr Gly Asn Pro Ser Asn Ser Trp
    210                 215                 220

Leu Ser Pro Thr Glu Pro Ser Ser Glu Thr Gly Asn Pro Arg His Leu
225                 230                 235                 240

His Val Leu Ile Gly Thr Ser Val Ile Ile Leu Phe Ile Leu Leu
                245                 250                 255

Leu Phe Phe Leu Leu His Arg Trp Cys Cys Asn Lys Lys Asn Ala Val
            260                 265                 270

Val Met Asp Gln Glu Pro Ala Gly Asn Arg Thr Val Asn Arg Glu Asp
        275                 280                 285

Ser Asp Glu Gln Asp Pro Gln Glu Val Thr Tyr Ala Gln Leu Asn His
    290                 295                 300

Cys Val Phe Thr Gln Arg Lys Ile Thr His Pro Ser Gln Arg Pro Lys
305                 310                 315                 320
```

```
Thr Pro Pro Thr Asp Ile Ile Val Tyr Thr Glu Leu Pro Asn Ala Glu
                325             330             335
Pro
```